US009352160B2

(12) United States Patent
Brooke

(10) Patent No.: US 9,352,160 B2
(45) Date of Patent: May 31, 2016

(54) METHOD AND APPARATUS FOR PHRENIC STIMULATION DETECTION

(71) Applicant: Cardiac Pacemakers, Inc., St. Paul, MN (US)

(72) Inventor: M. Jason Brooke, Baltimore, MD (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/665,690

(22) Filed: Mar. 23, 2015

(65) Prior Publication Data

US 2015/0190642 A1    Jul. 9, 2015

Related U.S. Application Data

(63) Continuation of application No. 14/157,571, filed on Jan. 17, 2014, now Pat. No. 8,996,112, which is a continuation of application No. 12/368,828, filed on Feb. 10, 2009, now Pat. No. 8,649,866.

(60) Provisional application No. 61/065,743, filed on Feb. 14, 2008.

(51) Int. Cl.
*A61N 1/18* (2006.01)
*A61N 1/37* (2006.01)
*A61B 5/00* (2006.01)
(Continued)

(52) U.S. Cl.
CPC .............. *A61N 1/371* (2013.01); *A61B 5/4029* (2013.01); *A61B 5/4848* (2013.01); *A61N 1/3601* (2013.01); *A61N 1/36585* (2013.01); *A61N 1/3712* (2013.01); *A61B 5/04001* (2013.01); *A61B 5/042* (2013.01); *A61B 5/0488* (2013.01); *A61B 5/1107* (2013.01);
(Continued)

(58) Field of Classification Search
None
See application file for complete search history.

(56) References Cited

U.S. PATENT DOCUMENTS 3,920,005 A    11/1975   Gombrich et al.
4,023,564 A     5/1977   Valiquette et al.
(Continued)

FOREIGN PATENT DOCUMENTS

EP    0468720 A2    1/1992
EP    0560569 A2    9/1993
(Continued)

OTHER PUBLICATIONS

"European Application Serial No. 09709478.3, Decision to Grant mailed Sep. 10, 2015", 2 pgs.
(Continued)

*Primary Examiner* — Brian T Gedeon
(74) *Attorney, Agent, or Firm* — Schwegman Lundberg & Woessner, P.A.

(57) ABSTRACT

Approaches for characterizing a phrenic stimulation threshold, a cardiac capture threshold, a maximum device parameter, and a minimum device parameter are described. A plurality of cardiac pacing pulses can be delivered by using a cardiac pacing device, a pacing parameter of the plurality of cardiac pacing pulses being changed between delivery of at least some of the pulses. One or more sensor signals can be evaluated to detect stimulation of the phrenic nerve by one or more of the plurality of cardiac pacing pluses. The evaluation of the one or more sensor signals and the pacing parameter can be compared to determine if a phrenic stimulation threshold is at least one of higher than a maximum device parameter and lower than a minimum device parameter.

20 Claims, 9 Drawing Sheets

(51) Int. Cl.
*A61N 1/36* (2006.01)
*A61N 1/365* (2006.01)
*A61B 5/04* (2006.01)
*A61B 5/042* (2006.01)
*A61B 5/0488* (2006.01)
*A61B 5/11* (2006.01)
*A61N 1/368* (2006.01)
*A61N 1/372* (2006.01)

(52) U.S. Cl.
CPC ...... *A61B 2562/0219* (2013.01); *A61N 1/3684* (2013.01); *A61N 1/372* (2013.01)

(56) References Cited

U.S. PATENT DOCUMENTS

| | | |
|---|---|---|
| 4,340,063 A | 7/1982 | Maurer |
| 4,364,396 A | 12/1982 | Barthel |
| 4,365,636 A | 12/1982 | Barker et al. |
| 4,458,692 A | 7/1984 | Simson |
| 4,476,869 A | 10/1984 | Bihn |
| 4,550,221 A | 10/1985 | Mabusth |
| 4,552,154 A | 11/1985 | Hartlaub |
| 4,562,841 A | 1/1986 | Brockway et al. |
| 4,573,481 A | 3/1986 | Bullara et al. |
| 4,648,407 A | 3/1987 | Sackner |
| 4,680,708 A | 7/1987 | Ambos et al. |
| 4,686,332 A | 8/1987 | Greanias et al. |
| 4,827,935 A | 5/1989 | Geddes et al. |
| 4,860,766 A | 8/1989 | Sackner |
| 4,878,497 A | 11/1989 | Callaghan et al. |
| 4,928,688 A | 5/1990 | Mower |
| 4,953,551 A | 9/1990 | Mehra et al. |
| 4,979,507 A | 12/1990 | Heinz et al. |
| 5,000,189 A | 3/1991 | Throne et al. |
| 5,033,467 A | 7/1991 | Bocchi et al. |
| 5,036,849 A | 8/1991 | Hauck et al. |
| 5,101,831 A | 4/1992 | Koyama et al. |
| 5,105,354 A | 4/1992 | Nishimura et al. |
| 5,133,353 A | 7/1992 | Hauser |
| 5,146,918 A | 9/1992 | Kallok |
| 5,170,784 A | 12/1992 | Ramon |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes et al. |
| 5,203,348 A | 4/1993 | Dahl et al. |
| 5,209,229 A | 5/1993 | Gilli et al. |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck |
| 5,324,310 A | 6/1994 | Greeninger |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,335,657 A | 8/1994 | Terry et al. |
| 5,350,410 A | 9/1994 | Kleks et al. |
| 5,353,788 A | 10/1994 | Miles et al. |
| 5,360,442 A | 11/1994 | Dahl et al. |
| 5,366,496 A | 11/1994 | Dahl et al. |
| 5,372,606 A | 12/1994 | Lang et al. |
| 5,374,280 A | 12/1994 | den Dulk |
| 5,376,106 A | 12/1994 | Stahmann et al. |
| 5,376,476 A | 12/1994 | Eylon et al. |
| 5,388,578 A | 2/1995 | Yomitov et al. |
| 5,391,200 A | 2/1995 | Kenknight |
| 5,397,342 A | 3/1995 | Heil, Jr. et al. |
| 5,411,031 A | 5/1995 | Yomtov et al. |
| 5,411,525 A | 5/1995 | Swanson et al. |
| 5,411,529 A | 5/1995 | Hudrlik et al. |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | Van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson et al. |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittmann et al. |
| 5,658,318 A | 8/1997 | Stroetmann |
| 5,662,688 A | 9/1997 | Haefner et al. |
| 5,662,696 A | 9/1997 | Kroll et al. |
| 5,674,254 A | 10/1997 | Van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff |
| 5,895,414 A | 4/1999 | Sanchez-Zambrano |
| 5,916,243 A | 6/1999 | Kenknight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarnarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |

(56) References Cited

U.S. PATENT DOCUMENTS

| | | |
|---|---|---|
| 6,076,015 A | 6/2000 | Hartley |
| 6,084,253 A | 7/2000 | Turner, Jr. |
| 6,091,973 A | 7/2000 | Colla et al. |
| 6,101,416 A | 8/2000 | Sloman |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | Kenknight |
| 6,148,234 A | 11/2000 | Struble |
| 6,163,724 A | 12/2000 | Hemming et al. |
| 6,169,921 B1 | 1/2001 | Kenknight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey |
| 6,238,419 B1 | 5/2001 | Lindgren |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,418,340 B1 | 7/2002 | Conley et al. |
| 6,418,343 B1 | 7/2002 | Zhang et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell |
| 6,615,083 B2 | 9/2003 | Küpper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij |
| 6,701,170 B2 | 3/2004 | Stetson |
| 6,708,058 B2 | 3/2004 | Kim et al. |
| 6,725,085 B2 | 4/2004 | Schwartzmann et al. |
| 6,731,973 B2 | 5/2004 | Voith |
| 6,731,983 B2 | 5/2004 | Ericksen et al. |
| 6,731,984 B2 | 5/2004 | Cho et al. |
| 6,731,985 B2 | 5/2004 | Poore et al. |
| 6,738,668 B2 | 5/2004 | Mouchawar et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,772,008 B2 | 8/2004 | Zhu |
| 6,773,404 B2 | 8/2004 | Poezevera et al. |
| 6,778,860 B2 | 8/2004 | Ostroff et al. |
| 6,782,291 B1 | 8/2004 | Bornzin et al. |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,884,218 B2 | 4/2005 | Olson et al. |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,907 B2 | 8/2005 | Bardy et al. |
| 6,944,495 B2 | 9/2005 | MacAdam et al. |

(56) References Cited

U.S. PATENT DOCUMENTS

| | | |
|---|---|---|
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Björling et al. |
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll |
| 6,993,389 B2 | 1/2006 | Ding |
| 6,999,817 B2 | 2/2006 | Park et al. |
| 7,006,869 B2 | 2/2006 | Bradley |
| 7,025,730 B2 | 4/2006 | Cho et al. |
| 7,027,861 B2 | 4/2006 | Thompson |
| 7,027,868 B2 | 4/2006 | Rueter et al. |
| 7,027,871 B2 | 4/2006 | Burnes et al. |
| 7,031,773 B1 | 4/2006 | Levine et al. |
| 7,039,459 B2 | 5/2006 | Bardy |
| 7,039,465 B2 | 5/2006 | Bardy |
| 7,043,299 B2 | 5/2006 | Erlinger |
| 7,050,851 B2 | 5/2006 | Plombon et al. |
| 7,062,327 B2 | 6/2006 | Bradley et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,081,095 B2 | 7/2006 | Lynn et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,094,207 B1 | 8/2006 | Koh |
| 7,096,064 B2 | 8/2006 | Deno et al. |
| 7,103,404 B2 | 9/2006 | Staler et al. |
| 7,107,093 B2 | 9/2006 | Burnes |
| 7,113,823 B2 | 9/2006 | Yonce et al. |
| 7,115,097 B2 | 10/2006 | Johnson |
| 7,117,036 B2 | 10/2006 | Florio |
| 7,120,495 B2 | 10/2006 | Bardy et al. |
| 7,123,960 B2 | 10/2006 | Ding |
| 7,127,290 B2 | 10/2006 | Girouard |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho |
| 7,177,689 B2 | 2/2007 | Ternes et al. |
| 7,179,229 B1 | 2/2007 | Koh |
| 7,181,285 B2 | 2/2007 | Lindh |
| 7,184,835 B2 | 2/2007 | Kramer et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al |
| 7,225,021 B1 | 5/2007 | Park et al. |
| 7,228,173 B2 | 6/2007 | Cazares |
| 7,233,821 B2 | 6/2007 | Hettrick et al. |
| 7,236,819 B2 | 6/2007 | Brockway |
| 7,242,978 B2 | 7/2007 | Cao |
| 7,242,983 B2 | 7/2007 | Frei et al. |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen et al. |
| 7,319,900 B2 | 1/2008 | Kim et al. |
| 7,330,761 B2 | 2/2008 | Zhang |
| 7,337,000 B2 | 2/2008 | Meyer et al. |
| 7,359,749 B2 | 4/2008 | Quenet et al. |
| 7,369,889 B2 | 5/2008 | Aström et al. |
| 7,392,086 B2 | 6/2008 | Sathaye |
| 7,426,412 B1 | 9/2008 | Schecter |
| 7,438,686 B2 | 10/2008 | Cho |
| 7,457,664 B2 | 11/2008 | Zhang et al. |
| 7,463,924 B2 | 12/2008 | Bardy et al. |
| 7,468,040 B2 | 12/2008 | Hartley |
| 7,477,932 B2 | 1/2009 | Lee |
| 7,499,751 B2 | 3/2009 | Meyer et al. |
| 7,509,170 B2 | 3/2009 | Zhang et al. |
| 7,519,423 B2 | 4/2009 | Begemann et al. |
| 7,558,628 B2 | 7/2009 | Yonce et al. |
| 7,574,260 B2 | 8/2009 | Stalsberg et al. |
| 7,580,741 B2 | 8/2009 | Cazares et al. |
| 7,587,240 B2 | 9/2009 | Zhang et al. |
| 7,617,002 B2 | 11/2009 | Goetz |
| 7,647,108 B2 | 1/2010 | Freeberg |
| 7,653,431 B2 | 1/2010 | Cazares et al. |
| 7,680,536 B2 | 3/2010 | Sathaye et al. |
| 7,684,861 B2 | 3/2010 | Sanders |
| 7,706,866 B2 | 4/2010 | Zhang et al. |
| 7,734,347 B2 | 6/2010 | Sathaye et al. |
| 7,738,959 B2 | 6/2010 | Manrodt et al. |
| 7,761,162 B2 | 7/2010 | Dong et al. |
| 7,765,004 B2 | 7/2010 | Stalsberg et al. |
| 8,185,202 B2 | 5/2012 | Sathaye |
| 8,260,421 B2 | 9/2012 | Sathaye |
| 8,649,866 B2 | 2/2014 | Brooke |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1 | 5/2002 | Sullivan et al. |
| 2002/0082658 A1 | 6/2002 | Heinrich et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2003/0023175 A1 | 1/2003 | Arzbaecher et al. |
| 2003/0135248 A1 | 7/2003 | Stypulkowski |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0208241 A1 | 11/2003 | Bradley et al. |
| 2003/0212436 A1 | 11/2003 | Brown |
| 2004/0064162 A1 | 4/2004 | Manrodt et al. |
| 2004/0082975 A1 | 4/2004 | Meyer et al. |
| 2004/0116978 A1 | 6/2004 | Bradley |
| 2004/0172065 A1 | 9/2004 | Sih et al. |
| 2004/0215253 A1 | 10/2004 | Weinberg |
| 2004/0215277 A1 | 10/2004 | Oosterhoff et al. |
| 2004/0230229 A1 | 11/2004 | Lovett |
| 2004/0260351 A1 | 12/2004 | Holmstrom et al. |
| 2005/0004612 A1 | 1/2005 | Scholten et al. |
| 2005/0010120 A1 | 1/2005 | Jung |
| 2005/0038478 A1 | 2/2005 | Klepfer et al. |
| 2005/0043652 A1 | 2/2005 | Lovett et al. |
| 2005/0060007 A1 | 3/2005 | Goetz |
| 2005/0065587 A1 | 3/2005 | Gryzwa |
| 2005/0085865 A1 | 4/2005 | Tehrani |
| 2005/0113710 A1 | 5/2005 | Stahmann et al. |
| 2005/0131476 A1 | 6/2005 | Kim et al. |
| 2005/0131477 A1 | 6/2005 | Meyer et al. |
| 2005/0131478 A1 | 6/2005 | Kim et al. |
| 2006/0069322 A1 | 3/2006 | Zhang et al. |
| 2006/0074331 A1 | 4/2006 | Kim et al. |
| 2006/0074454 A1 | 4/2006 | Freeberg |

(56) References Cited

U.S. PATENT DOCUMENTS

| | | | |
|---|---|---|---|
| 2006/0111747 | A1 | 5/2006 | Cazares et al. |
| 2006/0116593 | A1 | 6/2006 | Zhang et al. |
| 2006/0129193 | A1 | 6/2006 | Zhang |
| 2006/0129194 | A1 | 6/2006 | Zhang |
| 2006/0129195 | A1 | 6/2006 | Sathaye et al. |
| 2006/0129196 | A1 | 6/2006 | Dong et al. |
| 2006/0129197 | A1 | 6/2006 | Zhang et al. |
| 2006/0129198 | A1 | 6/2006 | Zhang |
| 2006/0129199 | A1 | 6/2006 | Zhang |
| 2006/0247693 | A1 | 11/2006 | Dong et al. |
| 2006/0247695 | A1 | 11/2006 | Stalsberg et al. |
| 2006/0253043 | A1 | 11/2006 | Zhang et al. |
| 2006/0253044 | A1 | 11/2006 | Zhang et al. |
| 2007/0049974 | A1 | 3/2007 | Li et al. |
| 2007/0055124 | A1 | 3/2007 | Viswanathan |
| 2007/0142741 | A1 | 6/2007 | Berthon-Jones et al. |
| 2007/0239057 | A1 | 10/2007 | Pu et al. |
| 2007/0255321 | A1 | 11/2007 | Gerber et al. |
| 2008/0004665 | A1 | 1/2008 | McCabe et al. |
| 2008/0009909 | A1 | 1/2008 | Sathaye et al. |
| 2008/0046019 | A1 | 2/2008 | Sathaye |
| 2008/0071318 | A1 | 3/2008 | Brooke |
| 2008/0234556 | A1 | 9/2008 | Brooke et al. |
| 2008/0294215 | A1 | 11/2008 | Sathaye |
| 2008/0300644 | A1 | 12/2008 | Sathaye |
| 2009/0030470 | A1 | 1/2009 | Holmstrom |
| 2009/0043351 | A1* | 2/2009 | Sathaye ............... A61N 1/3686 607/28 |
| 2009/0043352 | A1 | 2/2009 | Brooke |

FOREIGN PATENT DOCUMENTS

| | | | |
|---|---|---|---|
| EP | 0940155 | A2 | 9/1999 |
| EP | 1038498 | A2 | 9/2000 |
| EP | 1151718 | A2 | 11/2001 |
| EP | 1291038 | A2 | 3/2003 |
| EP | 1629863 | A2 | 3/2006 |
| WO | 9217240 | A1 | 10/1992 |
| WO | 9220402 | A1 | 11/1992 |
| WO | 9904841 | A1 | 2/1999 |
| WO | 0001438 | A1 | 1/2000 |
| WO | 0017615 | A2 | 3/2000 |
| WO | 0240097 | A1 | 5/2002 |
| WO | 0247761 | A2 | 6/2002 |
| WO | 02087696 | A1 | 11/2002 |
| WO | 03003905 | A1 | 1/2003 |
| WO | 03028550 | A2 | 4/2003 |
| WO | 2004026398 | A1 | 4/2004 |
| WO | 2004091720 | A2 | 10/2004 |
| WO | 2005058412 | A2 | 6/2005 |
| WO | 2005089865 | A2 | 9/2005 |
| WO | 2006065707 | A2 | 6/2006 |
| WO | 2007087025 | A1 | 8/2007 |
| WO | 2008005270 | A2 | 1/2008 |
| WO | 2009020639 | A1 | 2/2009 |

OTHER PUBLICATIONS

"European Application Serial No. 09709478.3, Examination Notification Art. 94(3) mailed Aug. 5, 2014", 4 pgs.
"European Application Serial No. 09709478.3, Office Action mailed Apr. 22, 2015", 6 pgs.
"European Application Serial No. 09709478.3, Office Action mailed Sep. 29, 2010", 2 pgs.
"European Application Serial No. 09709478.3, Response filed Oct. 12, 2010 to Office Action mailed Sep. 29, 2010", 1 pg.
"European Application Serial No. 09709478.3, Response filed Dec. 8, 2014 to Examination Notification Art. 94(3) mailed Aug. 5, 2014", 12 pgs.
"International Application Serial No. PCT/US2008/009488, International Preliminary Report on Patentability mailed Feb. 18, 2010", 7 pgs.
"International Application Serial No. PCT/US2008/009488, International Search Report mailed Dec. 12, 2008", 3 pgs.
"International Application Serial No. PCT/US2008/009488, Written Opinion mailed Dec. 12, 2008", 6 pgs.
"International Application Serial No. PCT/US2009/033687, International Search Report mailed Apr. 6, 2009", 4 pgs.
"International Application Serial No. PCT/US2009/033687, Written Opinion mailed Apr. 6, 2009", 8 pgs.
Acar et al., SVD-based on-line exercise ECG signal orthogonalization, IEEE Transactions on Biomedical Engineering, vol. 46, No. 3, Mar. 1999. Abstract only.
Ajilore et al., Nightcap: Laboratory and home-based evaluation of a portable sleep monitor, 32 Psychophysiology, 32-98, 1995. Abstract only.
Belouchrani et al., Blind Source Separation Based on Time-Frequency Signal Representations, IEEE Transactions on Signal Processing, vol. 46, No. 11, pp. 2888-2897, Nov. 1998.
Cohen et al.. Capture Management Efficacy in children and young adults with enocardial and unipolar epicardial systems. Eurospace, vol. 6, pp. 248-255, 2004.
Comon, Independent component analysis, A new concept?, Signal Processing, vol. 36, No. 3, pp. 287-314, Apr. 1994.
Gallois et al., Multi-Channel Analysis of the EEG Signals and Statistic Particularities for Epileptic Seizure Forecast, Second Joint EMBS/BMES Conference, pp. 208-215, Oct. 23-26, 2002.
Gradaus et al., Nonthoracotomy Implantable Cardioverter Defibrillator Placement in Children: Use of Subcutaneous Array Leads and Abdominally Placed Implantable Cardioverter Defibrillators in Children, Journal of Cardiovascular Electrophysiology, vol. 12, No. 3, pp. 356-360, Mar. 2001.
Hartz et al., New Approach to Defibrillator Insertion, Journal of Thoracic Cardiovascular Surgery, vol. 97, pp. 920-922, 1989.
Hyvärinen et al., Independent Component Analysis: A Tutorial, Helsinki University of Technology, Apr. 1999.
Kolettis et al., Submammary Implantation of a Cardiovascular-Defibrillator with a Nonthoracotomy Lead System, American Heart Journal, vol. 126, pp. 1222-1226, Nov. 1993.
Krahn et al., Recurrent syncope. Experience with an Implantable loop record, Cardiol. Clin. vol. 15(2), pp. 316-326, May 1997.
Leng et al., "Lead Configuration of Defibrillator Implantation in a Patient with Congenital Heart Disease and a Mechanical Prosthetic Tricuspid Valve", PACE, vol. 24, No. 8, pp. 1291-1292, Aug, 2001.
Park et al., Use of an Implantable Cardioverter Defibrillator in an Eight-Month-Old Infant with Ventricular Fibrillation Arising from a Myocardial Fibroma, PACE, vol. 22, No. 1, 99. 138-139, Jan. 1999.
Rieta et al., Atrial Activity Extraction Based on Blind Source Separation as an Alternative to QRST Cancellation for Atrial Fibrillation Analysis, Computers in Cardiology, vol. 27, pp. 67-72, 2000.
Schuder et al., Experimental Ventricular Defibrillation with an Automatic and Completely Implanted System, Trans. American Society Artif. Int. Organs, vol. 16, pp. 207-212, 1970.
Schuder et al., Transthoracic Ventricular Defibrillation in the Dog with Truncated and Untruncated Exponential Stimuli, IEEE Transitions on Bio-Medical Engineering, vol. BME-18, No. 6, pp. 410-415, Nov. 1971.
Schuder et al., Ventricular Defibrillation in the Dog Using Implanted and Partially Implanted Electrode Systems, American Journal of Cardiology, vol. 33, pp. 243-247, Feb. 1974.
Smits et al., Defibrillation Threshold (DFT) Model of a Fully Subcutaneous ICD System, Eurospace Supplements, vol. 2, Jun. 2001 at col. 778, p. B83.
Splett et al. "Determination of Pacing Capture in Implantable Defibrillators: Benefit of Evoked Response Detection Using RV Coil to Can Vector," PACE, vol. 23, 2000, pp. 1645-1650.
Stirbis et al., Optimizing of the Shape of Implanted Artificial Pacemakers, Kaunas Medical Institute, Translated from Meditsinskaya Tekhnika, No. 6, pp. 25-87, 1986.
Verrier et al., Sleep, dreams, and sudden death: the case for sleep as an autonomic stress test for the heart, 31 Cardiovascular Research 181-211, 1996.
Verrier et al., Sleep Related Cardiovascular Risk: New Home-Based Monitoring Technology for Improved Diagnosis and Therapy, 2 A.N. E. 158-175, 1997.

(56) References Cited

OTHER PUBLICATIONS

Waldemark et al., Detection of Apnea using Short Window FFT Technique and Artificial Neural Network, 3390 SPIE International Society for Optical Engineering 122-133, 1998. Partial Article.

Zarzoso et al., Blind Separation of Independent Sources for Virtually Any Source Probability Density Function, IEEE Transactions on Signal Processing, vol. 47, No. 9, pp. 2419-2432. Sep. 1999.

Zarzoso et al., Noninvasive Fetal Electrocardiogram Extraction: Blind Separation Versus Adaptive Noise Cancellation, IEEE Transactions on Biomedical Engineering. vol. 48, No. 1, pp. 12-18, Jan. 2001.

All Non-Patent Literature and Foreign Patent Documents Have Been Previously Uploaded in Parent U.S. Appl. No. 14/157,571, filed Jan. 17, 2014 and U.S. Appl. No. 12/368,828, filed Feb. 10, 2009.

\* cited by examiner

METHOD AND APPARATUS FOR PHRENIC STIMULATION DETECTION

This application is a continuation of U.S. patent application Ser. No. 14/157,571, filed Jan. 17, 2014, which is a continuation of U.S. patent application Ser. No. 12/368,828, filed Feb. 10, 2009, now U.S. Pat. No. 8,649,866, which claims the benefit of Provisional Patent Application Ser. No. 61/065,743 filed on Feb. 14, 2008, to which priority is claimed pursuant to 35 U.S.C. §119(e), all of which are incorporated herein by reference.

FIELD OF THE INVENTION

The present invention relates generally to cardiac devices and methods, and, more particularly, to characterization of capture and phrenic stimulation thresholds and device parameters.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management (CRM) devices have been developed that provide pacing stimulation to one or more heart chambers in an attempt to improve the rhythm and coordination of atrial and/or ventricular contractions. CRM devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dyssynchrony.

Pacemakers are CRM devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue, generating an evoked response that generates a propagating depolarization wave that results in a contraction of the heart chamber. If a pace pulse energy is too low, the pace pulses may not reliably produce a contractile response in the heart chamber and may result in ineffective pacing that does not improve cardiac function or cardiac output.

Pacing pulses can unintentionally stimulate nerves or muscles, even if the pulse energy is not sufficient to capture cardiac tissue. For example, a delivered pacing pulse may stimulate a patient's phrenic nerve, which runs proximate the heart and innervates the diaphragm.

The present invention provides methods and systems using phrenic stimulation algorithms and provides various advantages over the prior art.

SUMMARY OF THE INVENTION

The present invention involves approaches for using phrenic stimulation algorithms for characterization of capture and phrenic stimulation thresholds and device parameters. One embodiment of the invention is directed to a method comprising delivering a plurality of cardiac pacing pulses using a cardiac pacing device, a pacing parameter of the plurality of cardiac pacing pulses being changed between delivery of the pulses. The parameter can be a pacing pulse amplitude or width, for example. The method embodiment further includes evaluating one or more sensor signals to detect activation of the phrenic nerve by one or more of the plurality of cardiac pacing pulses and comparing the evaluation of the one or more sensor signals and the pacing parameter to determine if a phrenic nerve activation threshold is at least one of higher than a maximum device parameter and lower than a minimum device parameter. The cardiac capture threshold can be a detected minimum pacing pulse amplitude that causes depolarization in targeted cardiac tissue. The maximum device parameter can be a maximum width of a pacing pulse that the cardiac pacing device is programmed to deliver. The minimum device parameter can be a minimum width of a pacing pulse that the cardiac pacing device is programmed to deliver.

Another embodiment is directed to a cardiac rhythm management system, the system comprising an implantable cardiac pacing device having a plurality of electrodes. The implantable cardiac pacing device can include circuitry configured to output a plurality of cardiac pacing pulses through the electrodes and modify one or more pacing parameters of the plurality of cardiac pacing pulses, one or more sensors configured to sense activation of the phrenic nerve by one or more of the plurality of pacing pulses and provide one or more signals based on the sensed phrenic nerve activation, a controller configured to execute program instructions stored in memory to cause the system to compare the one or more signals and the one or more pacing parameters to determine if a phrenic nerve activation threshold is at least one of higher than a maximum cardiac pacing device parameter and lower than a minimum cardiac pacing device parameter, and store information based on the determination.

Another embodiment is directed to a cardiac rhythm management system, the system comprising an implantable cardiac pacing device having a plurality of electrodes. The implantable cardiac pacing device can include circuitry configured to output a plurality of cardiac pacing pulses through the plurality of electrodes and modify one or more pacing parameters of the plurality of cardiac pacing pulses, one or more sensors configured to sense activation of the phrenic nerve by one or more of the plurality of pacing pulses and provide one or more signals based on the sensed phrenic nerve activation, means for comparing the evaluation of the one or more sensor signals and the one or more pacing parameters to determine if a phrenic nerve activation threshold is at least one of higher than a maximum programmed device parameter and lower than a minimum programmed device parameter.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
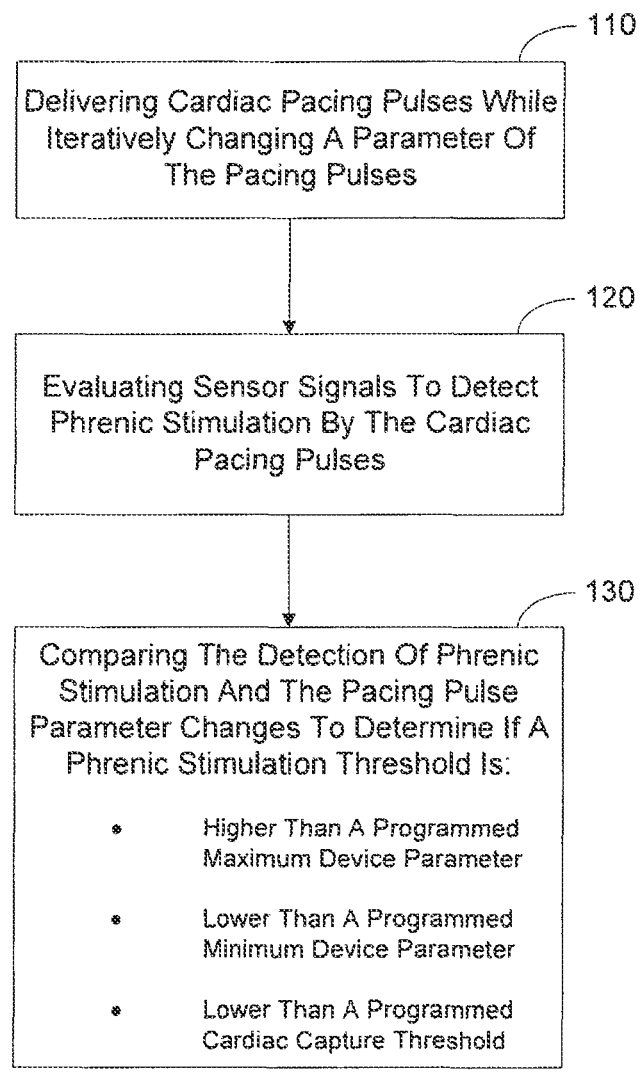
FIG. 1 is a flowchart illustrating a method of characterizing device parameter limits, capture thresholds, and phrenic stimulation thresholds in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices, or methods according to the present invention may include one or more of the features, structures, methods, or combinations thereof described herein. For example, a device or system may be implemented to include one or more of the advantageous features and/or processes described below. It is intended that such a device or system need not include all of the features described herein, but may be implemented to include selected features that provide for useful structures and/or functionality. Such a device or system may be implemented to provide a variety of therapeutic or diagnostic functions.

A wide variety of implantable cardiac monitoring and/or stimulation devices may be configured to implement phrenic stimulation algorithms of the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transveneous, endocardial, and epicardial electrodes (i.e., intrathoracic electrodes), and/or subcutaneous, non-intrathoracic electrodes, including can, header, and indifferent electrodes, and subcutaneous array(s) or lead electrodes (i.e., non-intrathoracic electrodes).

Bi-ventricular pacing provides therapy options for patients suffering from heart failure. However, new challenges have been presented by placement of the left-ventricular lead via the coronary sinus in bi-ventricular pacing systems. Due to the proximity of the coronary veins to the phrenic nerve, left ventricular pacing may result in phrenic nerve stimulation. The phrenic nerve innervates the diaphragm, so stimulation of the phrenic nerve can cause a patient to experience a hiccup. Electrical stimulation of the phrenic nerve can be uncomfortable for the patient, and can interfere with breathing. Therefore, phrenic stimulation from cardiac pacing may cause the patient to exhibit uncomfortable breathing patterns timed with the left-ventricular pace.

A phrenic stimulation threshold, above which the phrenic nerve will be stimulated by a pacing pulse, can be determined. One method for determining a phrenic stimulation threshold includes sensing for phrenic nerve activation and/or diaphragmic movement timed with the delivery of pacing pulses. If no phrenic stimulation is sensed using the level of electrical energy delivered, the energy level can be iteratively increased for subsequent trials of delivering electrical energy and monitoring for phrenic stimulation until phrenic stimulation is sensed. The electrical energy level at which phrenic stimulation is detected can be the phrenic stimulation threshold. In some embodiments, the level of electrical energy may be decreased or otherwise adjusted until phrenic stimulation is not detected. The energy delivered during such a scan could also be used to simultaneously perform other tests, such as searching for a capture threshold.

Methods for evaluating phrenic stimulation that may be incorporated in embodiments of the invention are disclosed in U.S. Pat. No. 6,772,008; and Patent Application Publication No. 20060241711, filed Apr. 26, 2005, each of which are herein incorporated by reference in their respective entireties.

Programming a pacing device to avoid undesirable stimulation, such as phrenic stimulation, is not one dimensional, as many other factors can be important in setting appropriate pacing parameters. For example, a pace pulse must exceed a minimum energy value, or capture threshold, to produce an intended contraction of cardiac tissue. It is desirable for a pace pulse to have sufficient energy to stimulate capture of the heart without expending energy significantly in excess of the capture threshold. Thus, accurate determination of the capture threshold provides efficient pace energy management. If the pace pulse energy is too low, the pace pulses may not reliably produce a contractile response in the heart and may result in ineffective pacing.

A capture threshold can be determined using, among other methods, a step-down technique where a capture threshold is identified when loss of capture is detected after successive pacing cycles. A step-up technique can also be used, whereby a capture threshold is identified when capture is detected after successive pacing cycles without capture. Capture can be detected using characteristics of an electrocardiogram indicating an intended cardiac response (e.g., a QRS complex).

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction. For example, embodiments of the invention can characterize capture and phrenic stimulation thresholds and deliver a back-up pulse with a higher energy level than a standard pacing energy level set at or above the capture threshold, the back-up pulse energy level below the phrenic stimulation threshold.

Pacing devices can have pacing parameter limits, such as programmed limits and limits on device capability. For example, an implantable pacing device may be programmed to only deliver pacing pulses not exceeding a specified amplitude. Other programmed limits can include minimum pulse amplitude, minimum pulse duration, maximum pulse duration, minimum pulse frequency, maximum pulse frequency, minimum pulse current, and/or maximum pulse current, among other parameters. Devices may be programmed with these and other parameter limits for several reasons. For example, a device programmed to automatically select a pacing pulse amplitude may have a programmed limit on the amplitude to prevent the device from selecting a pulse amplitude that could be dangerous to the patient (such as in an auto-capture mode). Additionally, a device may be programmed with parameter limits to avoid operating conditions that can harm the device.

Upon implantation of a pacing device, a human analyst, such as a doctor, may establish initial capture and phrenic nerve stimulation thresholds. Based on those initial threshold determinations, the analyst may program the device with parameter range limits within which automated device features can operate. In the case of pulse amplitude, a doctor may set a voltage range having a minimum above the capture threshold and a maximum below the phrenic stimulation threshold within which an autocapture feature can operate. The maximums and minimums may each have a safety margin such that the range between the parameter minimum/maximum is less than the range between the capture and phrenic stimulation thresholds. The safety margin provides some protection from an autocapture program pacing below the capture threshold or above the phrenic stimulation threshold if either of these thresholds were to change over time.

Devices can also have capability limits associated with the hardware of the device. For example, even if no programming limits are placed on the operation of a pacing device, the device may still have limits regarding minimum pulse amplitude, maximum pulse amplitude, minimum pulse duration, maximum pulse duration, minimum pulse frequency, maximum pulse frequency, minimum pulse current, and maximum pulse current, among other parameters. Device capability limits can be related to the performance limits of the components, such as capacitors and battery, used to construct the device.

In multi-electrode pacing systems, multiple pacing electrodes may be disposed in a single heart chamber, in multiple heart chambers, and/or elsewhere in a patient's body. Electrodes used for delivery of pacing pulses may include one or more cathode electrodes and one or more anode electrodes. Pacing pulses are delivered via the cathode/anode electrode combinations, where the term "electrode combination" denotes that at least one cathode electrode and at least one anode electrode are used. An electrode combination may involve more than two electrodes, such as when multiple electrodes that are electrically connected are used as the anode and/or multiple electrodes that are electrically connected are used as the cathode. Typically, pacing energy is delivered to the heart tissue via the cathode electrode(s) at one or more pacing sites, with a return path provided via the anode electrode(s). If cardiac capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing.

Pacing pulses may be applied through multiple electrodes (i.e., pacing vectors defined by various electrode combinations) in a single cardiac chamber in a timed sequence during the cardiac cycle to improve contractility and enhance the pumping action of the heart chamber. It is desirable for each pacing pulse delivered via the multiple electrode combinations to capture the cardiac tissue proximate the cathode electrode. Capture of cardiac tissue depends upon, among other things, the vector used to deliver the pulse and various pulse parameters, such as the amplitude and duration of the pulse.

Stimulation characteristics of a pacing therapy are dependent on many factors, including the distance between the electrodes, proximity to targeted tissue, proximity to non-targeted tissue susceptible to unintended stimulation, type of tissue contacting and between the electrodes, impedance between the electrodes, resistance between the electrodes, and electrode type, among other factors. Such factors can influence the cardiac capture and phrenic stimulation thresholds. Stimulation characteristics can vary with physiologic changes, electrode migration, physical activity level, body fluid chemistry, hydration, and disease state, among other factors. Therefore, the stimulation characteristics for each electrode combination are unique and can change over time. As such, it can be useful to periodically determine the stimulation characteristics (e.g., cardiac capture and phrenic stimulation thresholds) for each electrode combination for optimum pacing (e.g., pacing at or just above the cardiac capture threshold and not causing undesirable stimulation).

It can be useful to consider device parameter limitations in relation to various thresholds (e.g., phrenic stimulation, cardiac capture) when programming, reprogramming, and/or operating a device. For example, if it is known that the phrenic stimulation threshold is greater than a device pulse amplitude limit, then a device may not need to consider phrenic stimulation when performing a scan to update a cardiac capture threshold. Additionally, a step-up amplitude scan of an auto-capture procedure may use larger parameter increments to facilitate faster determination of a cardiac capture threshold if it is known that the phrenic stimulation threshold is higher than the programmed device limits. In a step-down scan mode, a device may alert a physician and/or perform a reconfiguration if it is determined that the device minimum parameter limits are above the phrenic stimulation threshold (e.g., the device cannot deliver a pacing pulse having a pulse width that does not stimulate the phrenic nerve).

Devices of the present invention may facilitate characterization of pacing configurations using various phrenic stimulation algorithms. A device may determine the relationship between device parameter limits, capture threshold, and/or phrenic stimulation threshold, among other things. Embodiments may notify a doctor and/or take some other action if changes in one or more of the thresholds might change the relationship between the programmed parameter limits and one or more of the thresholds. For example, a doctor might be notified and/or a device may be automatically reprogrammed (by itself or another system) if a phrenic stimulation threshold changes such that the threshold is lower than a programmed pacing parameter limit, where before the phrenic stimulation threshold was higher than the maximum parameter limit of the programmed range.

The flowchart of FIG. 1 illustrates a process for using a phrenic stimulation algorithm. The process includes delivering 110 cardiac pacing pulses while iteratively changing a parameter of the pacing pulses. The parameter iteratively changed could be one or more of pulse amplitude, width, frequency, and current, among other parameters. The parameter change could be an increase or decrease. In this way, a scan can be performed for each of the one or more parameters to investigate the physiological response (e.g., capture, phrenic stimulation) across at least a portion of the available parameter spectrum.

Sensor signals are evaluated 120 to detect phrenic stimulation by the delivered 110 cardiac pacing pulses. Phrenic stimulation can be detected by the methods disclosed herein. In one embodiment, phrenic stimulation could be detected by an accelerometer signal indicating thoracic movement (e.g., an induced hiccup) shortly after the delivery 110 of a pacing pulse. Phrenic stimulation can also be detected by the detection of a short-duration deviation in the amplitude of a transthoracic impedance signal.

Information regarding the evaluation 120 to detect phrenic stimulation and the delivery 110 of pacing pulses can be compared 130 to determine, among other things, if a phrenic stimulation threshold is higher than a maximum programmed device parameter, lower than a minimum programmed device parameter, and/or lower than cardiac capture threshold.

For example, if the evaluation 120 did not detect phrenic stimulation corresponding to any of the delivered 110 pacing pulses, even though a pacing pulse was delivered at the maximum programmed amplitude setting for a pacing device, then it can be identified that the phrenic stimulation threshold is greater than the device's maximum programmed amplitude parameter. Additionally, it may be determined that the phrenic stimulation pulse width threshold is greater than the device's maximum programmed pulse width parameter. Similar relationships could also be identified for the other parameters disclosed herein.

If the process of FIG. 1 is employed using a step-down iterative parameter change approach, then it may be identified that the phrenic stimulation threshold is below a device's programmed minimum amplitude and/or pulse width parameter. A step-down scan according to the process of FIG. 1 may also identify that a capture threshold is below a device's minimum programmed amplitude and/or pulse width parameter, that a phrenic stimulation threshold is greater than a cardiac capture threshold, and/or that either or both of the phrenic stimulation and cardiac capture thresholds are below a maximum programmed device parameter.

In some embodiments, a device may scan only within its programmed parameter range that a particular process, such as autocapture, is allowed to operate. Such embodiments minimize testing while ensuring that a threshold has not drifted into the programmed range of the automated process.

In some embodiments, a device may scan outside of its programmed parameter range within which a particular process is allowed to operate. Such embodiments allow a device and/or doctor to recognize when thresholds have changed relative to programmed parameter limits and take appropriate action. For example, if it is identified that a capture threshold has decreased and drifted further from a minimum programmed parameter limit, then a device may be reprogrammed with a lower minimum parameter limit, which can conserve battery life. If a phrenic stimulation threshold has decreased, then a device can be reprogrammed with a lower maximum parameter limit to ensure a safety margin exists between the phrenic stimulation threshold and the maximum programmed parameter limit.

Based on the identified relationships between the phrenic stimulation threshold, the capture threshold, and the various programmed pulse parameter limits, a doctor may be notified that reprogramming of the device is needed. For example, if it is determined that a capture threshold has increased over time then embodiments of the invention can facilitate notification to the doctor that the capture threshold has increased and is nearing a device's minimum programmed pulse amplitude parameter (where a scan had been performed outside of the programmed parameter limits). In such case the doctor may reprogram the pulse parameter limits of the device by increasing the minimum programmed pulse parameter. A doctor may further increase the maximum programmed pulse parameter to allow automated functions of the device, such as an autocapture process, adequate variability in changing a parameter. Alternatively, a device may reprogram itself or be programmed by another system to modify programmed parameter limits in response to identified changing relationships between the phrenic stimulation threshold, the capture threshold, and various programmed pulse parameter limits.

The various steps of FIG. 1, as well as the other steps disclosed herein, can be performed automatically, such that no direct human assistance (e.g., physician and/or patient) is needed to initiate or perform the various discrete steps. Alternatively, the various steps of this disclosure can be performed semi-automatically requiring some amount of human interaction to initiate or conduct one or more steps.

Figure 2:
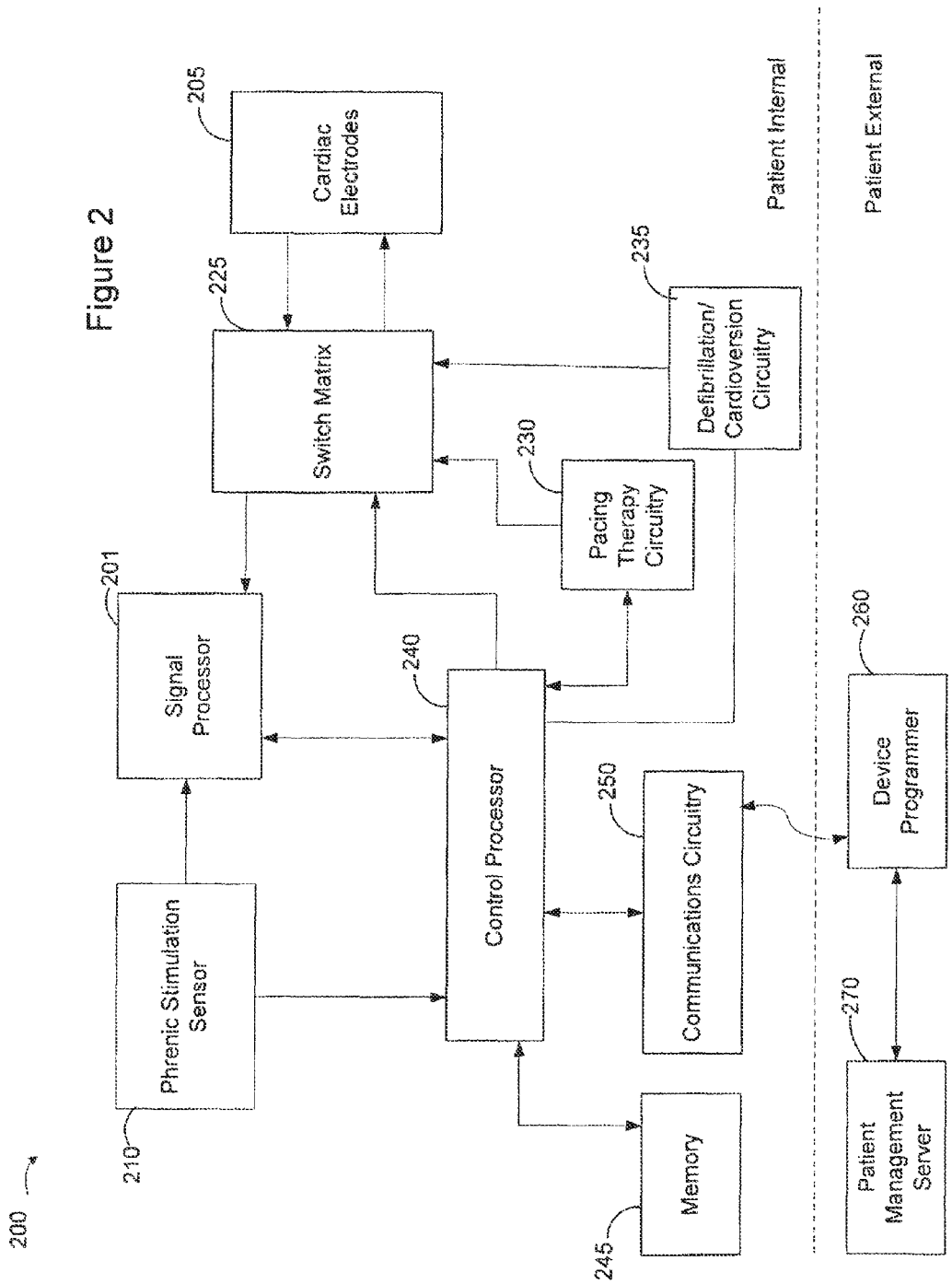
FIG. 2 is a block diagram of system circuitry in accordance with embodiments of the invention.

FIG. 2 is a block diagram of a CRM device 200 that may incorporate circuitry employing phrenic stimulation algorithms in accordance with embodiments of the present invention. The CRM device 200 includes pacing therapy circuitry 230 that delivers pacing pulses to a heart. The CRM device 200 may optionally include defibrillation/cardioversion circuitry 235 configured to deliver high energy defibrillation or cardioversion stimulation to the heart for terminating dangerous tachyarrhythmias.

The pacing pulses are delivered via multiple cardiac electrodes 205 (electrode combinations), which can be disposed at multiple locations within a heart, among other locations. Two or more electrodes may be disposed within a single heart chamber. The electrodes 205 are coupled to switch matrix 225 circuitry used to selectively couple electrodes 205 of various pacing configurations to signal processor 201 and/or other components of the CRM device 200.

The CRM device also includes a phrenic stimulation sensor 210. The phrenic stimulation sensor 210 can output a signal and/or other information to signal processor 201 and control processor 240. Phrenic stimulation sensor 210 may include an accelerometer, electrical signal sensors (e.g., EMG, impedance), pressure sensor, acoustic sensors, and/or any other sensor that can participate in the detection of phrenic stimulation. Phrenic stimulation sensor 210 may be implemented using a discrete sensor or via software executed by a processor (e.g., control processor 240) of the FRM device.

The control processor 240 can use information received from the signal processor 201, the phrenic stimulation sensor 210, memory 245, and other components to implement phrenic stimulation algorithms, as disclosed herein.

For example, the pacing therapy circuitry 230 can provide information regarding when a pacing pulse was delivered and the parameters of the pacing pulse, the phrenic stimulation sensor 210 can provide information regarding sensed phrenic stimulation, and signal processor can provide information regarding capture of the heart. This information can be used to determine, among other things, if a phrenic stimulation threshold is higher than a maximum device parameter, lower than a minimum device parameter, and/or lower than cardiac capture threshold, among other things.

Amplitude, peak timing, and/or correlation of delivered pulses to phrenic stimulation (beat-to-beat and/or over time) can be used with a phrenic stimulation signal in either the time or frequency domain to determine whether one or more pacing pulses caused phrenic stimulation.

A CRM device 200 typically includes a battery power supply (not shown) and communications circuitry 250 for communicating with an external device programmer 260 or other patient-external device. Information, such as data, parameter information, evaluations, comparisons, data, and/or program instructions, and the like, can be transferred between the device programmer 260 and patient management server 270, CRM device 200 and the device programmer 260, and/or between the CRM device 200 and the patient management server 270 and/or other external system. In some embodiments, the processor 240, memory 245, and/or signal processor 201 may be components of the device programmer 260, patient management server 270, and/or other patient external system.

The CRM device 200 also includes a memory 245 for storing executable program instructions and/or data, accessed by and through the control processor 240. In various configurations, the memory 245 may be used to store information related to thresholds, parameters, parameter limits, measured values, program instructions, and the like.

The circuitry represented in FIG. 2 can be used to perform the various methodologies and techniques discussed herein. Memory 245 can be a computer readable medium encoded with a computer program, software, firmware, computer executable instructions, instructions capable of being executed by a computer, etc. to be executed by circuitry, such as control processor 240. For example, memory 245 can be a computer readable medium storing a computer program, execution of the computer program by control processor 240 causing delivery of pacing pulses directed by the pacing therapy circuitry, reception of one or more signals from phrenic stimulation sensors 210 and/or signal processor 201 to identify, and establish relationships between, device parameter limits, capture thresholds, and phrenic stimulation thresholds in accordance with embodiments of the invention according to the various methods and techniques made known or referenced by the present disclosure. In similar ways, the other methods and techniques discussed herein can be performed using the circuitry represented in FIG. 2.

Figure 3:
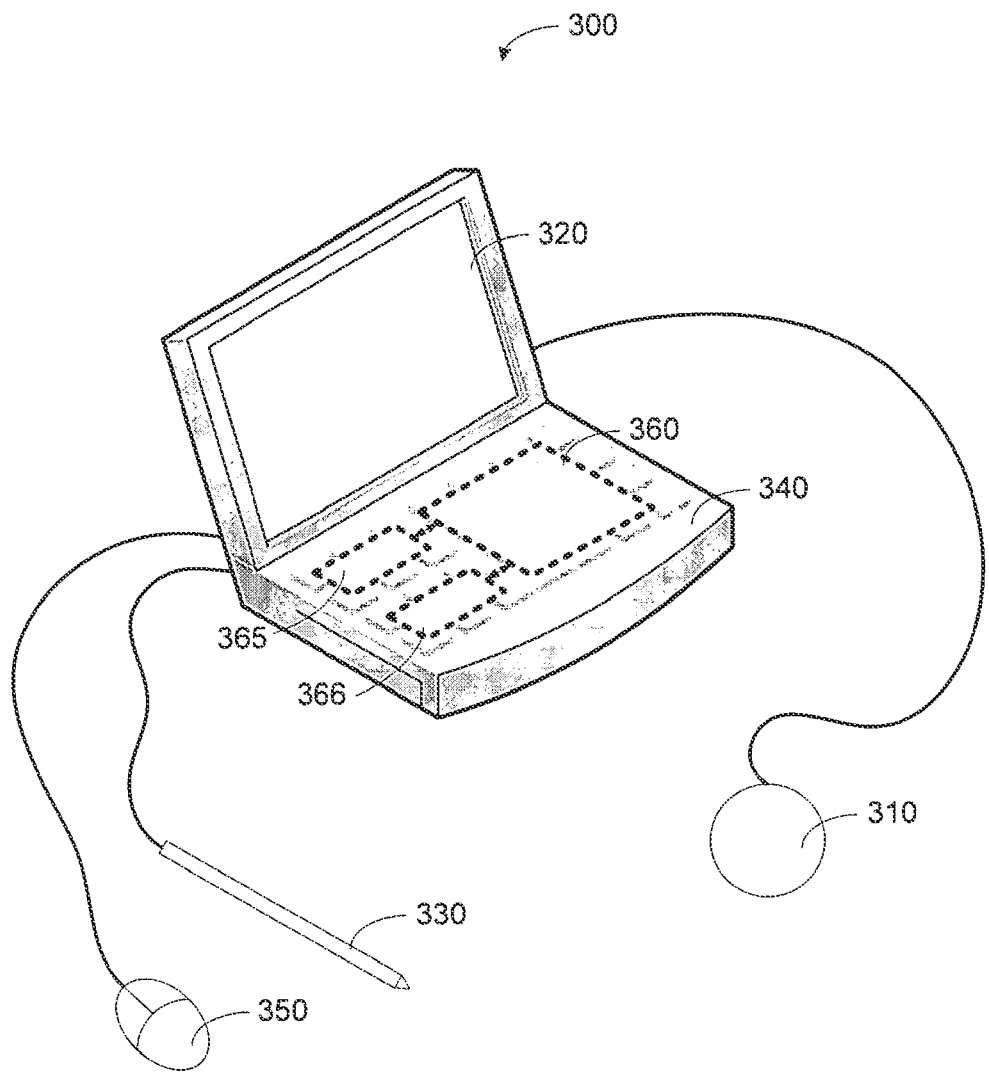
FIG. 3 is a diagram illustrating a patient-external device that provides a user interface allowing a human analyst to interact with information and program an implantable medical device in accordance with embodiments of the invention.

FIG. 3 illustrates a patient external device 300 that provides a user interface configured to allow a human analyst, such as a physician or patient, to interact with an implanted medical device. The patient external device 300 is described as a CRM programmer, although the methods of the invention are operable on other types of devices as well, such as portable telephonic devices, computers, PDA's, or patient information servers used in conjunction with a remote system, for example. The programmer 300 includes a programming head 310 which is placed over a patient's body near the implant site of an implanted device to establish a telemetry link between a CRM and the programmer 300. The telemetry link allows the data collected by the implantable device to be downloaded to the programmer 300. The downloaded data is stored in the programmer memory 365. In some embodiments, a communication link may be established between an implantable device and an external device via radio frequency, such that the implantable device and external device do not require relatively close proximity to facilitate transfer of data, commands, instructions, and other information.

The programmer 300 includes a graphics display screen 320, e.g., LCD display screen, that is capable of displaying graphics, alphanumeric symbols, and/or other information. For example, the programmer 300 may graphically display information regarding pacing parameters, device limits, sensed information, and thresholds downloaded from the CRM on the screen 320. The display screen 320 may include touch-sensitive capability so that the user can input information or commands by touching the display screen 320 with a stylus 330 or the user's finger. Alternatively, or additionally, the user may input information or commands via a keyboard 340 or mouse 350.

The programmer 300 includes a data processor 360 including software and/or hardware for performing the methods disclosed here, using program instructions stored in the memory 365 of the programmer 300. In one implementation, sensed data is received from a CRM via communications circuitry 366 of the programmer 300 and stored in memory 365. The data processor 360 evaluates the sensed data, which can include information related to pacing parameters, device limits, and thresholds. The data processor 360 can also perform other method steps discussed herein, including evaluating signals, detecting phrenic stimulation, and comparing pacing parameters, device limits, and thresholds, among other things. Pacing parameters, device limits, programmed parameter limits, and thresholds, as well as other information, may be presented to a user via a display screen 320. A notification regarding device pacing pulse parameter limits, capture threshold, and phrenic stimulation threshold can be displayed using the display screen 320 for review by a human analyst.

Figure 4:
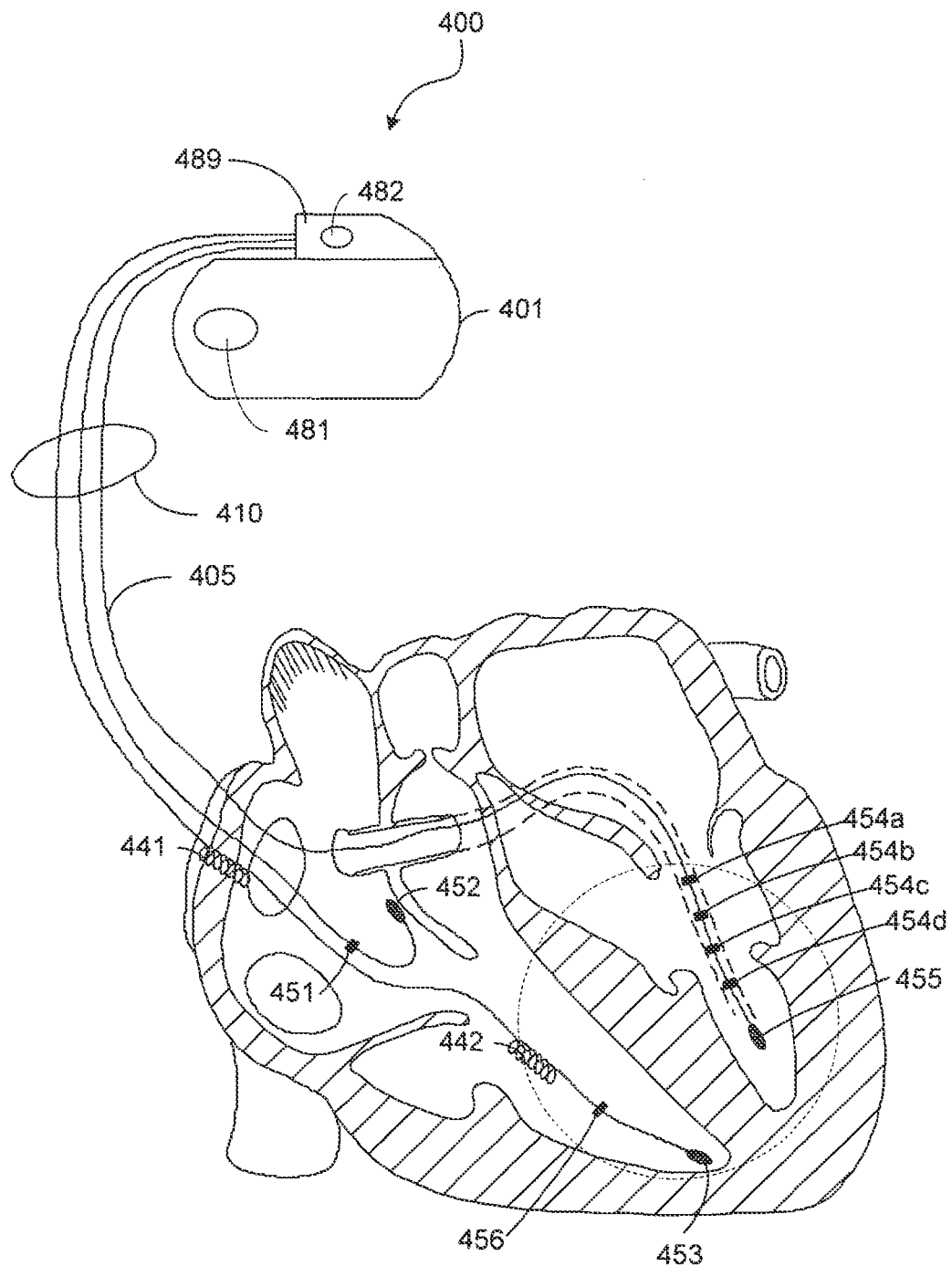
FIG. 4 is a therapy device incorporating circuitry capable of implementing electrode combination selection techniques in accordance with embodiments of the invention.

The therapy device 400 illustrated in FIG. 4 employs circuitry capable of implementing phrenic stimulation algorithm techniques described herein. The therapy device 400 includes CRM circuitry enclosed within an implantable housing 401. The CRM circuitry is electrically coupled to an intracardiac lead system 410. Although an intracardiac lead system 410 is illustrated in FIG. 4, various other types of lead/electrode systems may additionally or alternatively be deployed. For example, the lead/electrode system may comprise and epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 410 are shown inserted into the patient's heart. The lead system 410 includes cardiac pace/sense electrodes 451-456 positioned in, on, or about one or more heart chambers for sensing electrical signals from the patient's heart and/or delivering pacing pulses to the heart. The intracardiac sense/pace electrodes, such as those illustrated in FIG. 4, may be used to sense and/or pace one or more chambers of the heart, including the left ventricle, the right ventricle, the left atrium and/or the right atrium. The CRM circuitry controls the delivery of electrical stimulation pulses delivered via the electrodes 451-456. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy.

The lead system 410 may include defibrillation electrodes 441, 442 for delivering defibrillation/cardioversion pulses to the heart.

The left ventricular lead 405 incorporates multiple electrodes 454a-454d and 455 positioned at various locations within the coronary venous system proximate the left ventricle. Stimulating the ventricle at multiple locations in the left ventricle or at a single selected location may provide for increased cardiac output in patients suffering from heart failure (HF), for example, and/or may provide for other benefits. Electrical stimulation pulses may be delivered via the selected electrodes according to a timing sequence and output configuration that enhances cardiac function. Although FIG. 4 illustrates multiple left ventricle electrodes, in other configurations, multiple electrodes may alternatively or additionally be provided in one or more of the right atrium, left atrium, and right ventricle.

Portions of the housing 401 of the implantable device 400 may optionally serve as one or more multiple can 481 or indifferent 482 electrodes. The housing 401 is illustrated as incorporating a header 489 that may be configured to facilitate removable attachment between one or more leads and the housing 401. The housing 401 of the therapy device 400 may include one or more can electrodes 481. The header 489 of the therapy device 400 may include one or more indifferent electrodes 482. The can 481 and/or indifferent 482 electrodes may be used to deliver pacing and/or defibrillation stimulation to the heart and/or for sensing electrical cardiac signals of the heart.

Communications circuitry is disposed within the housing 401 for facilitating communication between the CRM circuitry and a patient-external device, such as an external programmer or advanced patient management (APM) system. The therapy device 400 may also include sensors and appropriate circuitry for sensing a patient's metabolic need and adjusting the pacing pulses delivered to the heart to accommodate the patient's metabolic need.

In some implementations, an APM system may be used to perform some of the processes discussed here, including evaluating, estimating, comparing, detecting, selecting, and updating, among others. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference in each of their respective entireties.

In certain embodiments, the therapy device 600 may include circuitry for detecting and treating cardiac tachyarrhythmia via defibrillation therapy and/or anti-tachyarrhythmia pacing (ATP). Configurations providing defibrillation capability may make use of defibrillation coils 441, 442 for delivering high energy pulses to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrode combinations within a heart chamber during different cardiac cycles.

Commonly owned U.S. Pat. No. 6,772,008, which is incorporated herein by reference, describes methods and systems that may be used in relation to detecting undesirable tissue stimulation. Muscle stimulation may be detected, for example, through the use of an accelerometer and/or other circuitry that senses accelerations indicating muscle movements that coincide with the output of the stimulation pulse.

Other methods of measuring tissue stimulation may involve, for example, the use of an electromyogram sensor (EMG), microphone, and/or other sensors. For example, stimulation of the laryngeal muscles may be automatically detected using a microphone to detect the patient's expiration response to undesirable diaphragmic activation due to electrical phrenic stimulation.

Undesirable nerve or muscle stimulation may be detected by sensing a parameter that is directly or indirectly responsive to the stimulation. Undesirable nerve stimulation, such as stimulation of the vagus or phrenic nerves, for example, may be directly sensed using electroneurogram (ENG) electrodes and circuitry to measure and/or record nerve spikes and/or action potentials in a nerve. An ENG sensor may comprise a neural cuff and/or other type or neural electrodes located on or near the nerve of interest. For example, systems and methods for direct measurement of nerve activation signals are discussed in U.S. Pat. Nos. 4,573,481 and 5,658,318 which are incorporated herein by reference in their respective entireties. The ENG may comprise a helical neural electrode that wraps around the nerve (e.g., phrenic nerve) and is electrically connected to circuitry configured to measure the nerve activity. The neural electrodes and circuitry operate to detect an electrical activation (action potential) of the nerve following application of the electrical stimulation pulse.

Neural activation can be detected by sensing a surrogate parameter that is indirectly responsive to nerve stimulation. Lung pressure, pleural pressure, thoracic pressure, airway pressure, and thoracic impedance are examples of parameters that change responsive to stimulation of the phrenic nerve. In some embodiments, a patient's airway pressure may be measured during and/or closely following delivery of electrical stimulation. The detected change in pressure may be related to stimulation of the phrenic nerve.

Undesirable stimulation threshold measuring may be performed by iteratively increasing, decreasing, or in some way changing a voltage, current, duration, energy level, and/or other therapy parameter between a series of test pulses. One or more sensors can monitor for undesirable activation immediately after each test pulse is delivered. Using these methods, the point at which a parameter change causes undesirable stimulation can be identified as an undesirable stimulation threshold.

By way of example and not by way of limitation, the undesirable stimulation threshold for a particular electrode combination may be measured by delivering first test pulse using the initial electrode combination. During and/or after each test pulse is delivered, sensors can monitor for undesirable stimulation. For example, an accelerometer may monitor for movement of the diaphragm indicating that the test pulse stimulated the phrenic nerve and/or diaphragm muscle. If no phrenic nerve and/or diaphragm muscle stimulation is detected after delivery of a test pulse, then the test pulse is increased a predetermined amount and another test pulse is delivered. This scanning process of delivering, monitoring, and incrementing is repeated until phrenic nerve and/or diaphragm muscle stimulation is detected. One or more of the test pulse parameters at which the first undesirable stimulation is detected can be considered to be the undesirable stimulation threshold.

Figure 5:
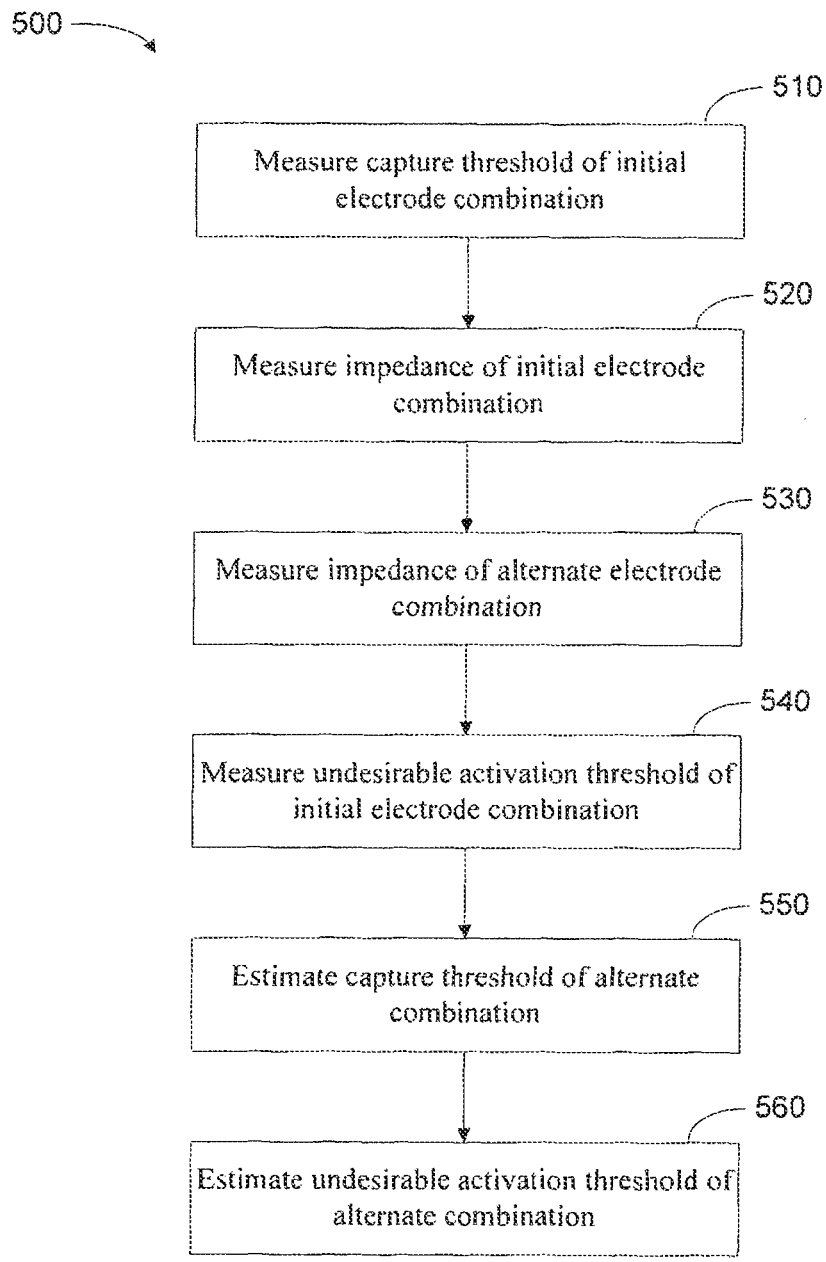
FIG. 5 is a flowchart illustrating a method of estimating thresholds in accordance with embodiments of the invention.

Although methods to measure cardiac capture and phrenic stimulation thresholds are disclosed herein, it is contemplated that various thresholds can be estimated instead of directly measured, as demonstrated in FIG. 5.

The flowchart of FIG. 5 illustrates a process 500 for estimating thresholds, such as a cardiac capture threshold or phrenic stimulation threshold. The process 500 includes measuring 510 a capture threshold of an initial electrode combination. The procedure for measuring 510 a capture threshold for the initial electrode combination can be done according to any capture threshold measuring methods disclosed herein or known in the art.

The process 500 of FIG. 5 further includes measuring 520 the impedance of the initial electrode combination. The impedance of the initial electrode combination may be measured with the capture threshold measurement of the initial electrode combination.

Any method for measuring impedance for one or more electrode combinations may be used. One illustrative example of techniques and circuitry for determining the impedance of an electrode combination is described in commonly owned U.S. Pat. No. 6,076,015 which is incorporated herein by reference in its entirety.

In accordance with this approach, measurement of impedance involves an electrical stimulation source, such as an exciter. The exciter delivers an electrical excitation signal, such as a strobed sequence of current pulses or other measurement stimuli, to the heart between the electrodes. In response to the excitation signal provided by an exciter, a response signal, e.g., voltage response value, is sensed by impedance detector circuitry. From the measured voltage response value and the known current value, the impedance of the electrode combination may be calculated.

The process 500 of FIG. 5 further includes measuring 530 the impedance of an alternate electrode combination. The measuring step 530 could be repeated for a plurality of different alternate electrode combinations.

The process 500 of FIG. 5 further includes measuring 540 an undesirable activation threshold (e.g., phrenic stimulation threshold) of the initial electrode combination. The procedure for measuring 540 the undesirable activation threshold of the initial electrode combination may be similar to the procedure for measuring 510 the capture threshold of the initial electrode combination, and may be done concurrently with the measuring 510 of the capture threshold of the initial electrode combination.

The process 500 of FIG. 5 further includes estimating 550 a capture threshold of the alternate electrode combination. Estimating 550 the capture threshold of the alternate electrode combination can be performed by using the capture threshold and the impedance of the initial electrode combination and the impedance of the alternate electrode combination.

Estimation of the capture threshold of the alternate electrode combination in accordance with some embodiments described herein, is based on the assumption that for a given pulse width, the capture threshold voltage for the initial electrode combination and the capture threshold voltage for the alternate electrode combination require an equal amount of current, energy or charge. The relationship between the capture threshold voltage and current for each electrode combination can be defined by Ohm's law as follows:

$$V_{th} = I_{th} Z, \qquad [1]$$

where $V_{th}$ is the capture threshold voltage of the electrode combination, $I_{th}$ is the capture threshold current of the electrode combination, and $Z$ is the impedance of the electrode combination.

For the initial electrode combination, the relationship between the capture threshold voltage and current may be expressed as:

$$V_{th\text{-}in} = I_{th\text{-}in} Z_{in} \qquad [2]$$

where, $V_{th\text{-}in}$ is the capture threshold voltage of the initial electrode combination, $I_{th\text{-}in}$ is the capture threshold current of the initial electrode combination, and $Z_{in}$ is the impedance of the initial electrode combination.

For the alternate electrode combination, the relationship between the capture threshold voltage and current may be expressed as:

$$V_{th\text{-}ex} = I_{th\text{-}ex} Z_{ex} \qquad [3]$$

where, $V_{th\text{-}ex}$ is the capture threshold voltage of the alternate electrode combination, $I_{th\text{-}ex}$ is the capture threshold current of the alternate electrode combination, and $Z_{ex}$ is the impedance of the alternate electrode combination.

As previously stated, in some embodiments, the capture threshold current of two electrode combinations having a common electrode is assumed to be about equal, or, $I_{th\text{-}in} = I_{th\text{-}ex}$.

The relationship between the alternate and initial capture threshold voltages may then be expressed as:

$$V_{th\text{-}ex} = \frac{V_{th\text{-}in}}{Z_{in}} Z_{ex} \qquad [4]$$

By the processes outlined above $V_{th\text{-}in}$, $Z_{in}$, and, $Z_{ex}$ are measured parameters, and the capture threshold voltage may be estimated based on these measured parameters.

The accuracy of an estimation calculation of a capture threshold for a particular electrode combination may be increased if the measured electrode combination has the same polarity as the electrode combination for which the capture threshold is being estimated. Methods for parameter estimation, including capture threshold estimation, are disclosed in U.S. patent application Ser. No. 11/505,645, filed on Aug. 17, 2006, herein incorporated by reference in its entirety.

The process 500 of FIG. 5 further includes estimating 560 an undesirable activation threshold of the alternate electrode combination. The undesirable activation threshold can be a phrenic stimulation threshold, for example. Estimating 560 the undesirable activation threshold of the alternate electrode combination can be performed by using the undesirable activation threshold and the impedance of the initial electrode combination and the impedance of the alternate electrode combination. Estimating 550 the undesirable activation threshold of the alternative electrode combination can be performing using methods similar to estimating a capture threshold, as discussed and referenced herein.

Estimating a threshold, such as estimating a capture threshold and/or an undesirable activation threshold, instead of measuring the same, can provide several advantages. For example, in some circumstances, measuring and estimating of some thresholds for a plurality of electrode combinations can be done faster than measuring the threshold for each electrode combination of a plurality of electrode combinations, as one or more test pulses do not need to be delivered for each electrode combination. Additionally, a test pulse can be uncomfortable for a patient to experience, and therefore minimizing the number of test pulses can be preferable.

The methods and devices disclosed herein can employ strength-duration relationship information measured or otherwise provided.

Capture is produced by pacing pulses having sufficient energy to produce a propagating wavefront of electrical depolarization that results in a contraction of the heart tissue. Generally speaking, the energy of the pacing pulse is a product of two energy parameters—the amplitude of the pacing pulse and the duration of the pulse. Thus, the capture threshold voltage over a range of pulse widths may be expressed in a capture strength-duration plot 610 as illustrated in FIG. 6.

Undesirable activation by a pacing pulse is also dependent on the pulse energy. The phrenic stimulation strength-duration plot 620 for undesirable activation may have a different characteristic from the capture strength-duration and may have a relationship between pacing pulse voltage and pacing pulse width.

A CRM device, such as a pacemaker, may have the capability to adjust the pacing pulse energy by modifying either or both the pulse width and the pulse amplitude to produce capture. Identical changes in pacing pulse energy may cause different changes when applied to identical therapies using different electrode combinations. Determining a capture strength-duration plot 610 can aid in characterizing the relationships between device parameter limits, capture threshold, and/or phrenic stimulation threshold, among other things.

Figure 6:
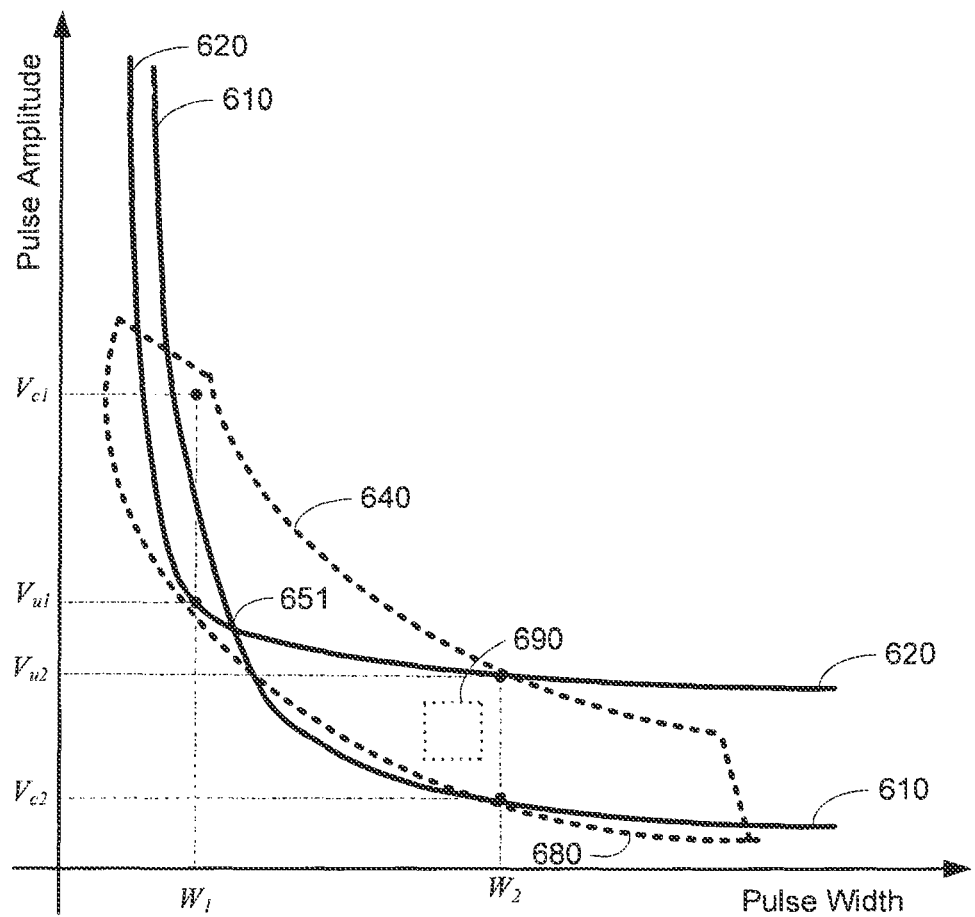
FIG. 6 is a graph illustrating various aspects of strength-duration pacing pulse parameter and device limit curves in accordance with embodiments of the invention.

FIG. 6 provides graphs illustrating a capture strength-duration plot 610 associated and a phrenic stimulation strength-duration plot 620 associated with an undesirable diaphragmic activation. A pacing pulse having a pulse width of $W_1$ requires a pulse amplitude of $V_{c1}$ to produce capture. A pacing pulse having pulse width $W_1$ and pulse amplitude $V_{c1}$ exceeds the voltage threshold, $V_{u1}$, for an undesirable diaphragmic activation. If the pulse width is increased to $W_2$, the voltage required for capture, $V_{c2}$, is less than the voltage required for undesirable diaphragmic activation, $V_{u2}$. Therefore, pacing pulses can be delivered at the pacing energy associated with $W_2$, $V_{c2}$ to provide capture of the heart without causing the phrenic stimulation.

The area to the right of the intersection 651 of the capture and phrenic stimulation strength-duration plots 610, 620, between the phrenic stimulation strength-duration 620 and capture strength-duration 610 plots, defines a set of energy parameter values that produce capture while avoiding phrenic stimulation. Pacing pulses within this region produce the most ideal therapy response (capture without undesirable stimulation).

The capture and phrenic stimulation strength-duration plots 610, 620 of FIG. 6 may be generated by delivering a number of test pulses at various amplitudes and pulse widths and evaluating whether cardiac capture and undesirable stimulation occurred. The capture and phrenic stimulation strength-duration plots 610, 620 curves can then be completed by interpolation and extrapolation based on, for example, an exponential fit. Such methods can minimize the number of test pulses required to fully characterize the relationships between pulse parameters and stimulation, thereby minimizing battery consumption and uncomfortable testing.

Extrapolation and interpolation can also allow the relationships between pulse parameters and stimulation for a particular device configuration to be characterized beyond what the device itself is programmed to, or capable of, performing.

Dashed line curves 640 and 680 illustrate device capability pacing parameter limits. Maximum curve 640 illustrates the maximum energy output (based on pulse amplitude and width parameters) that the device is capable of delivering. Maximum curve 640 demonstrates a pulse parameter tradeoff for a particular device when attempting to deliver the maximum amount of energy possible—pulse amplitude is sacrificed for greater pulse width.

Minimum curve 680 illustrates the minimum energy output (based on pulse amplitude and width parameters) that the device is capable of delivering. A device can be capable of delivering pulses having amplitudes and pulse widths parameters within the area between the curves 640 and 680.

As demonstrated in FIG. 6, a particular device may not be capable of delivering a pacing pulse having any particular amplitude/width parameters that will capture the targeted cardiac tissue without causing undesirable stimulation.

It is generally desirable to have the greatest amount of overlap between the ranges of pacing pulse parameters that capture targeted cardiac tissue without causing undesirable stimulation and the ranges of pacing pulse parameters that a particular device is actually capable of delivering, as the amount of overlap reflects the relative amount of variation in parameters that can be used to achieve an intended therapy outcome.

The methods and devices discussed herein can facilitate understanding the relationships between device parameter limits, capture threshold, and/or phrenic stimulation threshold and optimizing a therapy. For example, the generation of the plots of FIG. 6 can allow for a comparison of overlap between the ranges of pulse parameters that capture targeted cardiac tissue without causing undesirable stimulation and the ranges of pulse parameters that a particular device is actually capable of delivering for different device configurations. A physician (or program) may elect to use the device configuration (e.g., electrode combination corresponding to a vector) having the greatest amount of overlap, as this configuration would likely correspond to the configuration having the greatest amount of flexibility in operation as the possible parameter ranges that achieve a desired therapy outcome are greatest.

Establishing the relationships between device parameter limits, capture threshold, and/or phrenic stimulation threshold can also aid is selecting pacing parameters. For example, when selecting a pulse width parameter, a physician may view a plot similar to that of FIG. 6 to select the pulse width that has the greatest amplitude range, the range being limited by the maximum device parameter curve 640, the minimum device parameter curve 680, the undesirable activation threshold curve 620, and/or the capture threshold curve 610. Likewise, a pulse amplitude parameter may be selected based on which pulse amplitude corresponds to the greatest pulse width range within the maximum device parameter curve 640, the minimum device parameter curve 680, the undesirable activation threshold curve 620, and/or the capture threshold curve 610. Parameter selection in this way may be performed by a human or automatically by a processor executing program instructions.

Methods and systems for determining and using strength-duration relationships are described in United States Patent Application Publication No. 2008/0071318, filed Sep. 14, 2006, which is incorporated herein by reference in its entirety.

FIG. 6 also illustrates programmed parameter limits 690 defining maximum and minimum pulse widths and amplitudes within which a device is programmed to operate. Various automated device features can automatically change pulse parameters to adjust to various conditions, such as with an autocapture program. A doctor may implement programmed parameter limits 690 to ensure that a device does not automatically adjust a parameter to a level that could be detrimental to patient care, such as to a level that prematurely runs down a battery or risks causing undesirable stimulation.

Programmed parameter limits 690 may be preprogrammed or set at device implantation based on detected threshold levels. If embodiments of the invention identify changing relationships between programmed parameter limits 690, the capture strength-duration plot 610, and the phrenic stimulation strength-duration plot 620, the programmed parameter limits 690 may be adjusted, either automatically or after a doctor is notified of the change, for example. Adjustment of programmed parameter limits 690 may increase a maximum pulse amplitude, decrease a maximum pulse amplitude, increase a minimum pulse amplitude, decrease a minimum pulse amplitude, increase a maximum pulse duration, decrease a maximum pulse duration, increase a minimum pulse duration, and/or decrease a minimum pulse duration. In such a way, a programmed parameter limit range, such as amplitude range, may be widened, narrowed, and/or shifted within the parameter limits 640 and 680 that the device is capable of delivering by reprogramming. Other pulse parameters limits of other pulse parameters discussed herein or otherwise made known may be similarly reprogrammed.

In some embodiments of the invention, identification of changing relationships between thresholds and programmed pulse limits may cause the device to modify automated processes that use pulse parameter increments and/or scanning techniques, such as autocapture. For example, if the phrenic stimulation strength-duration plot 620 was to decrease over time corresponding to a detected decrease in phrenic stimulation threshold, then an autocapture program may employ smaller parameter increments when operating within the programmed parameter limits 690. Alternatively, if the phrenic stimulation strength-duration plot 620 was to increase over time corresponding to a detected increase in phrenic stimulation threshold, then autocapture parameter increments may be increased. Increases in increments can facilitate faster identification of thresholds and the like while minimizing the delivery of test pulses. Decreases in increments can allow for more cautious and thorough scanning Increasing or decreasing pulse increments in response to changes in relationships between programmed parameter limits and thresholds can quickly optimize automated device functions while balancing safety, efficacy, and battery consumption considerations. Changes in parameter increments may be made automatically by a device upon detection of a change in relationship between programmed parameter limits and thresholds and/or implemented by a doctor upon reviewing information regarding the identified change in relationship.

In some embodiments, a capture threshold and/or phrenic stimulation threshold may be periodically identified and updated. If some amount of parameter separation exists between the programmed parameter limits and one or both of the thresholds then a device may retest to identify the capture threshold and/or phrenic stimulation threshold less frequently. The separation can be a preprogrammed safety margin between thresholds and programmed parameter limits. If a detected threshold is identified as within the parameter separation (e.g., exceeding the safety margin) then a device may increase the frequency with which it tests the thresholds. Increasing and/or decreasing the frequency of testing based on proximity of detected thresholds to programmed parameter limits can minimize battery consumption and uncomfortable testing while balancing safety and efficacy considerations (i.e., testing is done more frequently when it is likely that a threshold will drift into the programmed parameter limits and less frequently when a large margin exists between a threshold and the programmed limits).

Figure 7:
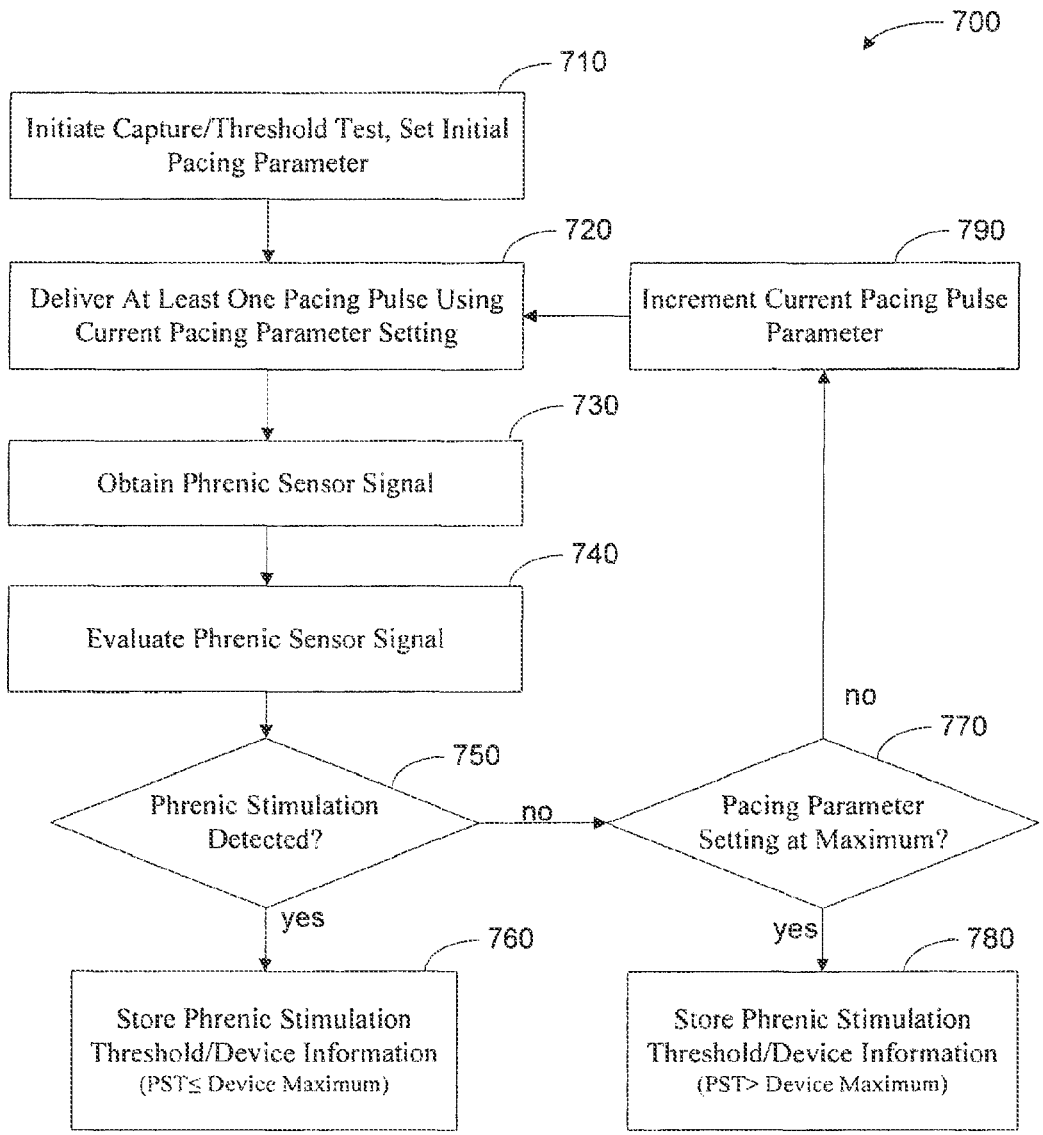
FIG. 7 is a flowchart illustrating a method characterizing device parameter limits, capture thresholds, and phrenic stimulation thresholds using a step-up scanning technique in accordance with embodiments of the invention.

The flowchart of FIG. 7 illustrates a process 700 for using phrenic stimulation algorithms for identifying, and characterizing the relationships between, device parameter limits, capture threshold, and/or phrenic stimulation threshold, among other things. The process 700 includes initiating 710 a capture/threshold test and setting an initial pacing parameter. The initial pacing parameter setting can be, for example, a device minimum amplitude, a device minimum pulse width, a device minimum pulse current, a previously determined capture threshold, or some combination thereof. The process 700 further includes delivering 720 at least one pacing pulse using the current pacing parameter setting. The current pacing parameter setting can be the initial pacing parameter setting if step 720 is being performed for the first time. Otherwise, the current pacing parameter setting can be a parameter value (e.g., pulse amplitude) different from that of the initial setting value.

After delivery 720 of the at least one pacing pulse, a phrenic sensor signal can be obtained 730. Such a phrenic sensor signal can be any signal produced by any sensor that is capable of detecting phrenic stimulation. The phrenic sensor signal is then evaluated 740. The evaluation 740 can be used to determine whether a delivered 720 pacing pulse stimulated the phrenic nerve or otherwise cause diaphragmic movement. If phrenic stimulation is detected 750, then phrenic stimulation threshold/device information is stored 760. Such information can reflect that the phrenic stimulation threshold (PST) is less than a device maximum parameter value, and may be equal to the device parameter minimum value or capture threshold, if the parameter value had been accordingly set and increased.

If phrenic stimulation is not detected 750, then it is determined whether the pacing parameter setting is set at a maximum value 770. During the first few iterations of the process 700, it is unlikely that the pacing parameter setting is set at a maximum value 770, and in which case the process 700 increments 790 the current pacing pulse parameter and returns to delivering 720 at least one more pacing pulse using the current pacing parameter setting. In this way, the process 700 can repeat steps 720-730-740-750-770-790, increasing the pacing pulse parameter each iteration in a scanning fashion until a phrenic stimulation threshold is identified 750-760 or the pacing parameter setting reaches a maximum 770.

If the pacing parameter setting is incremented 790 to a maximum 770, then the process 700 stores 780 phrenic stimulation threshold/device information. Such phrenic stimulation threshold/device information could reflect that the PST is greater than the maximum device parameter setting.

The capture threshold and/or PST for a particular electrode combination may change over time due to various physiological effects. Testing the capture threshold and PST for a particular electrode combination may be implemented periodically or on command to ensure that the information regarding relationships between device parameter limits, capture threshold, and/or phrenic stimulation threshold is current.

Figure 8:
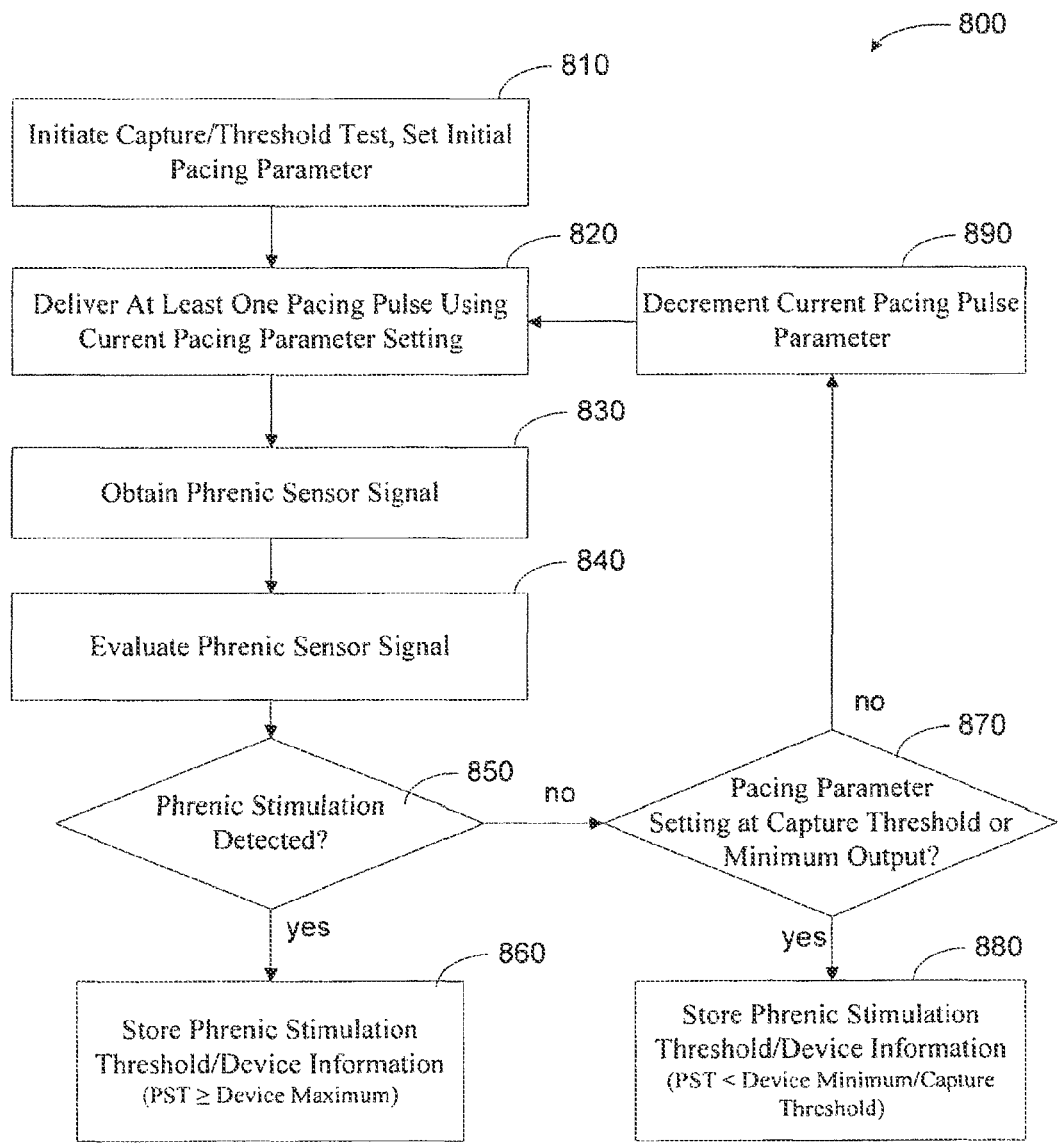
FIG. 8 is a flowchart illustrating a method of characterizing device parameter limits, capture thresholds, and phrenic stimulation thresholds using a step-down scanning technique in accordance with embodiments of the invention.

The flowchart of FIG. 8 illustrates a process 800 for using phrenic stimulation algorithms for identifying, and characterizing the relationships between, device parameter limits, capture threshold, and/or phrenic stimulation threshold, among other things. The process 800 includes initiating 810 a capture/threshold test and setting an initial pacing parameter. The initial pacing parameter setting can be, for example, a device maximum amplitude, a device maximum pulse width, a device maximum pulse current, a previously determined threshold, or some combination thereof. The process 800 further includes delivering 820 at least one pacing pulse using the current pacing parameter setting. The current pacing parameter setting can be the initial pacing parameter setting if step 820 is being performed for the first time. Otherwise, the current pacing parameter setting can be a parameter value (e.g., pulse amplitude) different from that of the initial setting value.

After delivery 820 of the at least one pacing pulse, a phrenic sensor signal can be obtained 830. Such a phrenic sensor signal can be any signal produced by any sensor that is capable of detecting phrenic stimulation. The phrenic sensor signal is then evaluated 840. The evaluation 840 can be used to determine whether a delivered 820 pacing pulse stimulated the phrenic nerve. If phrenic stimulation is detected 850 then phrenic stimulation threshold/device information is stored 860. Such information can reflect that the PST is greater than or equal to a device maximum parameter value.

If phrenic stimulation is not detected 850, then it is determined whether the pacing parameter setting is set at a minimum value and/or capture threshold 870. During the first few iterations of the process 800, it is unlikely that the pacing parameter setting is set at a minimum value or capture threshold 870, and in which case the process 800 decrements 890 the current pacing pulse parameter and returns to delivering 820 at least one more pacing pulse using the current pacing parameter setting. In this way, the process 800 can repeat steps 820-830-840-850-870-890, decreasing the pacing pulse parameter each iteration in a scanning fashion until a phrenic stimulation threshold is identified 850-860 or the pacing parameter setting reaches a device minimum and/or capture threshold 870. In some embodiments, it may be desirable to not scan for the phrenic stimulation threshold below the capture threshold as it could be dangerous to lose capture of cardiac tissue during the test.

If the pacing parameter setting is decremented 890 to a device minimum and/or capture threshold 870, then the process 800 stores 880 phrenic stimulation threshold/device information. Such phrenic stimulation threshold/device information could reflect that the PST is less than the minimum device parameter setting and/or cardiac capture threshold. If the testing fails to identify pacing parameters that produce capture and avoids phrenic stimulation, then an alert may be communicated to the external device via communication circuitry to alert a system or physician.

Figure 9:
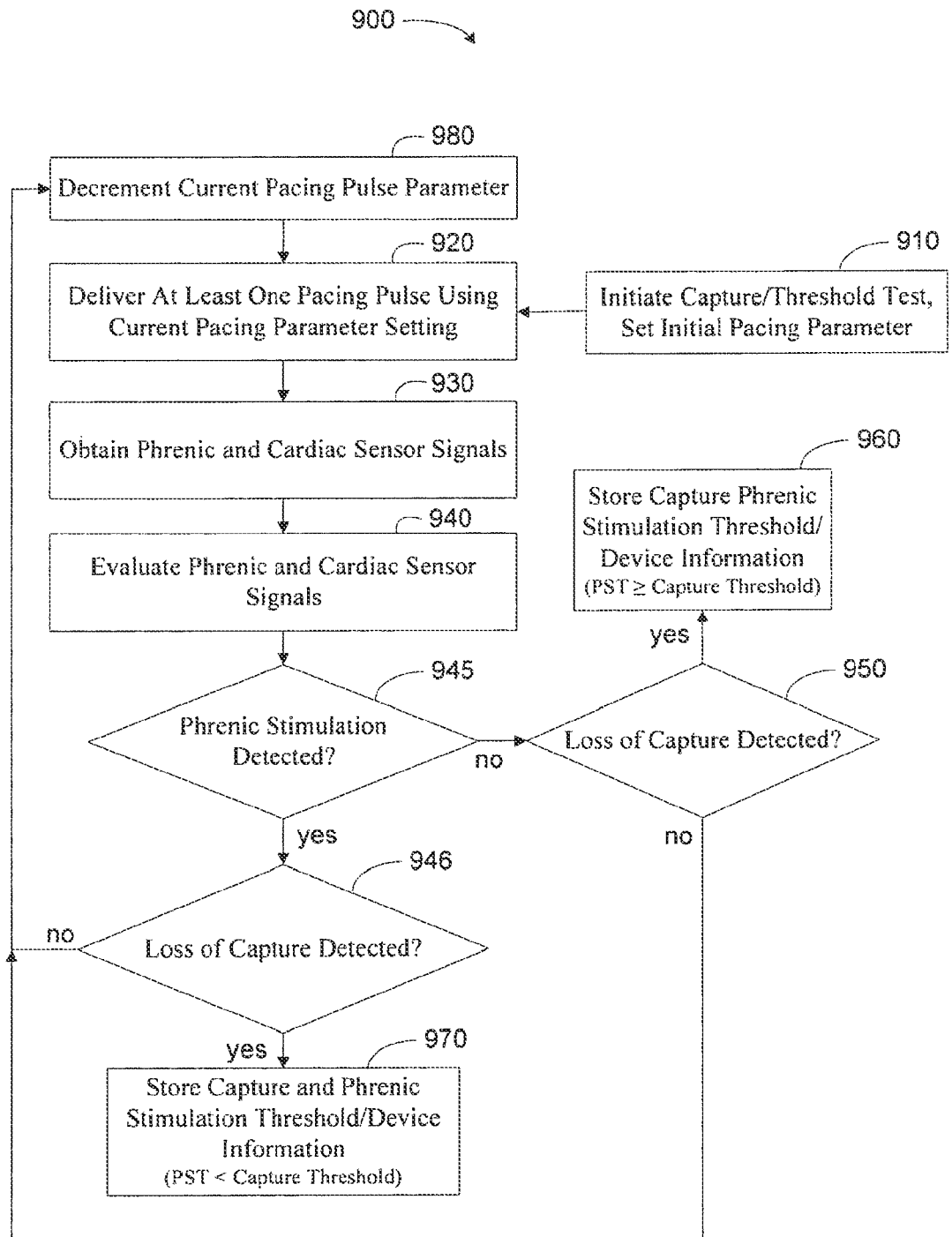
FIG. 9 is a flowchart illustrating a method of characterizing a capture threshold and phrenic stimulation threshold using a step-down scanning technique in accordance with embodiments of the invention.

The flowchart of FIG. 9 illustrates a process 900 for using phrenic stimulation algorithms for identifying, and characterizing the relationships between, device parameter limits, capture threshold, and/or phrenic stimulation threshold, among other things. The process 900 includes initiating 910 a capture/threshold test, and setting an initial pacing parameter. The initial pacing parameter setting can be, for example, a device maximum amplitude, a device maximum pulse width, a device maximum pulse current, a previously determined threshold, or some combination thereof. The process 900 further includes delivering 920 at least one pacing pulse using the current pacing parameter setting. The current pacing parameter setting can be the initial pacing parameter setting if step 920 is being performed for the first time. Otherwise, the current pacing parameter setting can be a parameter value (e.g., pulse amplitude) different from that of the initial setting value.

After delivery 920 of the at least one pacing pulse, a phrenic sensor signal and cardiac sensor signal can be obtained 930. Such phrenic and cardiac sensor signals can be any of the signals produced by sensors that are capable of detecting phrenic stimulation or detecting cardiac capture. The phrenic sensor signal and cardiac sensor signal are then evaluated 940. The evaluation 940 can be used to determine 945 whether a delivered 920 pacing pulse stimulated the phrenic nerve. If phrenic stimulation is detected 945 then the process 900 determines whether capture was lost 946 during the delivery 920 of the one or more pacing pulses.

If phrenic stimulation 945 and loss of cardiac capture 946 are both detected then cardiac capture and phrenic stimulation threshold/device information can be stored 970. Such information can reflect that the phrenic stimulation threshold PST is less than the capture threshold.

If phrenic stimulation is detected 945 and loss of capture is not detected 946 then the current pacing pulse parameter is decremented 980. For example, if the pacing pulse parameter is pulse width, then the current pulse width can be decremented 980 to a shorter pulse width. Pulse amplitude, frequency, and/or current pulse parameters can be similarly decremented (or incremented, in step-up embodiments).

If phrenic stimulation is not detected 945, the process 900 determines whether loss of capture was detected 950. If no phrenic stimulation is detected 945 and loss of capture is detected 950, then capture and phrenic stimulation threshold/device information is stored 960. Such information can indicate that the phrenic stimulation threshold is greater than or equal to the capture threshold.

In this way, the process 900 can repeat steps 920-930-940-945-946-980, or steps 920-930-940-945-950, decreasing the pacing pulse parameter each iteration in a scanning fashion until a relationship between phrenic stimulation threshold is the capture threshold is identified (e.g., PST>capture threshold or PST<capture threshold). Such a process allows for the simultaneous scanning for both a phrenic stimulation threshold and the cardiac capture threshold. Searching for these parameters together minimizes the number of pulses that need to be delivered, as compared to doing the tests separately, preserving battery energy and minimizing patient discomfort. Simultaneous scanning in this way also minimizes the total time necessary for a device to test to establish these thresholds.

The processes 700, 800, and 900, as well as other methods discussed herein, can be initiated upon implant, by a physician, upon detection of a change in condition, and/or periodically. Condition changes that could initiate the processes include loss of capture, change in posture, change in disease state, detection of non-therapeutic activation, and/or short or long term change in patient activity state, for example.

The device parameter limits of FIGS. 7, 8, and 9, and well as others discussed herein, can be programmed parameter limits or parameter limits corresponding to maximum/minimum pulse parameter values that a pacing system is capable of delivering.

Periodic and/or condition initiated testing to update capture threshold, phrenic stimulation threshold, and device relationship information can be useful to monitor for certain conditions that might not otherwise be readily apparent but warrant attention and/or a therapy change. Device and/or physiologic changes may alter the effect of pacing pulses. For example, device component defects, lead migration, electrode encapsulation, and/or physiologic changes may increase the pacing pulse amplitude needed to reliably produce capture and/or decrease the pacing pulse amplitude needed to stimulate the phrenic nerve, leading to uncomfortable and ineffective pacing therapy. Updated capture threshold, phrenic stimulation threshold, and device relationship information can be used to automatically reprogram the therapy device and/or alert a physician to reconfigure the therapy device.

The various processes illustrated and/or described herein (e.g., the processes of FIGS. 1, 5, 7, 8, and 9 and those associated with FIG. 6) can be performed using a single device embodiment (e.g., device of FIGS. 2 and 4) configured to perform each of the processes discussed herein.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising;
   delivering a pulse with a predetermined pulse energy;
   determining if the delivered pulse produced phrenic stimulation;
   if it is determined that the delivered pulse did not produce phrenic stimulation, performing a capture threshold test without performing a phrenic stimulation threshold test; and
   if it is determined that the delivered pulse did produce phrenic stimulation, performing a capture threshold test and a phrenic stimulation threshold test.

2. The method of claim 1, wherein the predetermined pulse energy corresponds to a cardiac pacing device capability limit.

3. The method of claim 1, wherein the predetermined pulse energy corresponds to a programmed cardiac pacing device limit.

4. The method of claim 1, wherein a cardiac pacing device includes a plurality of electrode combinations where each electrode combination defines a pacing vector, the method comprising performing the method for each of two or more pacing vectors.

5. The method of claim 4, further comprising:
   for each of the two or more pacing vectors, displaying on a display of a patient external device an indication of whether the pulse produced phrenic stimulation; and
   for each of the two or more pacing vectors, displaying on the display of the patient external device an indication of a capture threshold as determined by the capture threshold test.

6. The method of claim 1, wherein the capture threshold test comprises:
   delivering a plurality of cardiac pacing pulses; and
   changing a pacing parameter for one or more of the plurality of cardiac pacing pulses between delivery of at least some of the plurality of cardiac pacing pulses until a capture threshold is detected.

7. The method of claim 6, wherein the pacing parameter comprises an amplitude and/or width of a cardiac pacing pulse, and wherein the pacing parameter is reduced between delivery of at least some of the plurality of cardiac pacing pulses until the capture threshold is detected.

8. The method of claim 6, wherein the phrenic stimulation threshold test comprises:
   delivering a plurality of cardiac pacing pulses;
   changing a pacing parameter for one or more of the plurality of cardiac pacing pulses between delivery of at least some of the plurality of cardiac pacing pulses until the phrenic stimulation threshold is detected.

9. The method of claim 8, wherein at least some of the plurality of cardiac pacing pulses are part of both the capture threshold test and the phrenic stimulation threshold test.

10. The method of claim 1, wherein the phrenic stimulation threshold test comprises:
    delivering a plurality of cardiac pacing pulses; and
    changing a pacing parameter for one or more of the plurality of cardiac pacing pulses between delivery of at least some of the plurality of cardiac pacing pulses until a phrenic stimulation threshold is detected.

11. The method of claim 10, wherein the pacing parameter comprises an amplitude and/or width of a cardiac pacing pulse, and wherein the pacing parameter is reduced between delivery of at least some of the plurality of cardiac pacing pulses until the until the phrenic stimulation threshold is detected.

12. The method of claim 10, wherein the pacing parameter comprises an amplitude and/or width of a cardiac pacing pulse, and wherein the pacing parameter is increased between delivery of at least some of the plurality of cardiac pacing pulses until the until the phrenic stimulation threshold is detected.

13. The method of claim 1, wherein determining if the pulse produced phrenic stimulation comprises monitoring an output of an accelerometer secured relative to a patient.

14. The method of claim 1, wherein the method is performed at least in part by an implantable cardiac pacing device.

15. The method of claim 1, wherein the method is performed at least in part by a patient external device.

16. A method, comprising;
    (a) selecting an electrode combination of a plurality of electrode combinations;
    (b) delivering a pulse with a predetermined pacing pulse energy via the selected electrode combination;
    (c) determining if the pulse produced phrenic stimulation;
    (d) if it is determined that the pulse did not produce phrenic stimulation, perform a capture threshold test using the selected electrode combination without performing a phrenic stimulation threshold test;
    (e) if it is determined that the pulse did produce phrenic stimulation, perform a capture threshold test and a phrenic stimulation threshold test using the selected electrode combination; and
    (f) repeating steps (a)-(e) for at least one other electrode combination of the plurality of electrode combinations.

17. The method of claim 16, further comprising:
    displaying a capture threshold as determined by the capture threshold test for the selected electrode combination on a display of a patient external device.

18. The method of claim 16, further comprising:
    If the phrenic stimulation threshold test was performed, displaying a phrenic stimulation threshold as determined by the phrenic stimulation threshold test for the selected electrode combination on a display of a patient external device.

19. A medical apparatus, comprising;
    a pulse generator for generating pulses at selectable pulse energy;
    a controller operatively coupled to the pulse generator, the controller configured to:
    (a) instruct the pulse generator to deliver a pulse with a predetermined pacing pulse energy;
    (b) determine if the delivered pulse produced phrenic stimulation;

(c) if it is determined that the delivered pulse did not produce phrenic stimulation, perform a capture threshold test without performing a phrenic stimulation threshold test; and
(d) if it is determined that the delivered pulse did produce phrenic stimulation, perform a capture threshold test and a phrenic stimulation threshold test.

20. The medical apparatus of claim 19, further comprising:
a switch for selectively connecting the pulse generator to a selected electrode combination of a plurality of electrode combinations; and
wherein the controller is configured to repeat (a)-(d) for at least one other electrode combination of the plurality of electrode combinations.

* * * * *